US008778690B2

(12) United States Patent
Sailor et al.

(10) Patent No.: US 8,778,690 B2
(45) Date of Patent: Jul. 15, 2014

(54) POROUS OPTICAL SENSOR WITH FIDUCIAL MARKER AND METHOD FOR DETECTION OF ANALYTES

(75) Inventors: Michael J. Sailor, La Jolla, CA (US); Anne M. Ruminski, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 90 days.

(21) Appl. No.: 13/222,957

(22) Filed: Aug. 31, 2011

(65) Prior Publication Data

US 2012/0058567 A1   Mar. 8, 2012

Related U.S. Application Data

(60) Provisional application No. 61/378,442, filed on Aug. 31, 2010.

(51) Int. Cl.
*G01N 21/78* (2006.01)
*G01N 21/75* (2006.01)

(52) U.S. Cl.
USPC ............ 436/101; 436/164; 436/111; 436/124

(58) Field of Classification Search
USPC .......................... 436/101, 111, 124, 100, 106
See application file for complete search history.

(56) References Cited

U.S. PATENT DOCUMENTS

| | | | |
|---|---|---|---|
| 5,318,676 | A | 6/1994 | Sailor et al. |
| 6,105,878 | A | 8/2000 | Robinson et al. |
| 6,291,597 | B1 | 9/2001 | Gruber et al. |
| 6,720,177 | B2 | 4/2004 | Ghadiri et al. |
| 6,806,543 | B2 | 10/2004 | Yamakawa et al. |
| 6,970,239 | B2 | 11/2005 | Chan et al. |
| 7,001,669 | B2 | 2/2006 | Lu et al. |
| 7,042,570 | B2 | 5/2006 | Sailor et al. |
| 7,094,464 | B2 | 8/2006 | Mao et al. |
| 2001/0044119 | A1 | 11/2001 | Ghadiri et al. |
| 2002/0072116 | A1 | 6/2002 | Bhatia et al. |
| 2002/0132101 | A1 | 9/2002 | Fonash et al. |
| 2002/0167118 | A1 | 11/2002 | Billiet et al. |
| 2003/0089899 | A1 | 5/2003 | Lieber et al. |
| 2003/0171257 | A1 | 9/2003 | Stribl et al. |
| 2003/0231304 | A1 | 12/2003 | Chan et al. |
| 2004/0053422 | A1 | 3/2004 | Chan et al. |
| 2005/0042764 | A1 | 2/2005 | Sailor et al. |
| 2005/0058416 | A1 | 3/2005 | Hoon Lee et al. |
| 2005/0266045 | A1 | 12/2005 | Canham et al. |
| 2006/0096922 | A1 | 5/2006 | Gin et al. |
| 2006/0105043 | A1 | 5/2006 | Sailor |
| 2006/0236436 | A1 | 10/2006 | Li et al. |
| 2008/0145513 | A1 | 6/2008 | Li et al. |
| 2008/0212068 | A1* | 9/2008 | Sailor et al. ............ 356/36 |

FOREIGN PATENT DOCUMENTS

WO   WO 2004/071949   8/2004

OTHER PUBLICATIONS

Ruminski, Anne Marie, Manipulation of Surface Chemistry and Nanostructure Porous Silicon-Based Chemical Sensors, 2009, University of California, San Diego, ProQuest LLC.*
Allcock, P., et. al., "Time-resolved sensing of organic vapors in low modulation porous silicon dielectric mirrors", *Journal of Applied Physics*, vol. 90, No. 10, Nov. 15, 2001.
Allongue, P., "Porous silicon formation mechanisms", Aug. 1997.
Bellet, D., "Drying of Porous Silicon", *Properties of Porous Silicon*, vol. 18, (e. L. Canahm) pp. 38-43, (Short Run Press Ltd., London) 1997.
Berger, M.G., et. al., "Dielectric filters made of PS: advanced performance by oxidation and new layer structures", *Thin Solid Films*, 297 (1997) pp. 237-240.
Bley, R.A., et. al., "Characterization of Silicon Nanoparticles Prepared from Porous Silicon", *Chem. Mater.*, 1996, 8, 1881.
Canham, L.T., et. al, "Bioactive Silicon Structure Fabrication Through Nanoetching Techniques", *Adv. Matter*, 1995, 7, 1033.
Canham, L.T., "Storage of porous silicon", *Properties of Porous Silicon*, vol. 18, (e. L. Canahm) pp. 44-50, (Short Run Press Ltd., London) 1997.
Canham, L.T., et. al. "Derivatized Porous Silicon Mirrors: Implantable Optical Components with Slow Resorbability", *Phys. Stat. Sol. A* 2000, 182,521.
Chan, S., et. al., "Porous Silicon Microcavities for Biosensing Applications", *phys. stat. sol. (a)*, 182, 541, (2000).
Chan, Selena, et. al., "Identification of Gram Negative Bacteria Using Nanoscale Microcavities", *J. Am. Chem. Soc.*, (2001), 123, pp. 11797-11798.
Cunin, Frederique, et al., "Biomolecular screening with encoded porous silicon photonic crystals", www.nature.com/naturematerials, vol. 1, Sep. 2002, pp. 39-41.
Cazzanelli, M., et. al., "Temperature dependence of the photoluminescence of all-porous-silicon optical microcavities", *Journal of Applied Physics*, vol. 85, No. 3, Feb. 1, 1999.
Coffer, J.L., "Porous Silicon Formation By Stain Etching", *Properties of Porous Silicon*, vol. 18, (e. L. Canahm) pp. 23-29, (Short Run Press Ltd., London), 1997.
Dancil, Keiki-Pua S., et. al., "A Porous Silicon Optical Biosensor: Detection of Reversible Binding of IgG to a Protein A-Modified Surface", *J. Am. Chem. Soc.* 1999, 121, 7925.
Gao, Jun, et. al., "Porous-silicon vapor sensor based on laser interferometry", *Applied Physics Letters*, vol. 77, No. 6, Aug. 7, 2000.

(Continued)

*Primary Examiner* — Christine T Mui
(74) *Attorney, Agent, or Firm* — Greer, Burns & Crain Ltd.

(57) ABSTRACT

The invention provides a porous sensor and sensing methods that use a porous sensor with a porous nanostructure having an optical response and having a portion of the porous nanostructure filled with a fiducial marker that is non-reactive to an analyte of interest. In a preferred sensing method, reflectance spectra from both the fiducial marker and reactive portions of the porous structure are acquired simultaneously. The fiducial marker provides an internal reference that permits compensation for humidity, as well as off angle measurements. In addition, simple visual observations can reveal the presence of an analyte, including human observations.

24 Claims, 13 Drawing Sheets

(56) References Cited

OTHER PUBLICATIONS

Gao, Jun, et. al. "Vapor Sensors Based on Optical Interferometry from Oxidized Macroporous Silicon Films", *Langmuir*, 2002, 18, pp. 2229-2233.

Foraker, Amy B., et. al., "Microfabricated Porous Silicon Particles Enhance Paracellular Delivery of Insulin across Intestinal Caco-2 Cell Monolayers", *Pharm. Res.* 2003, 20,110.

Halimaoui, A., "Porous Silicon Formation by Anodisation", *Properties of Porous Silicon*, vol. 18, (e. L. Canahm) pp. 12-22, (Short Run Press Ltd., London), 1997.

Heinrich, J.L., et. al., "Luminescent Colloidal Silicon Suspensions from Porous Silicon", *Science*, 1992, 255, 66.

Lehmann, Volker, et. al., "Optical shortpass filters based on macroporous silicon", *Applied Physics Letters*, vol. 78, No. 5, Jan. 29, 2001.

Letant, S.E., et. al, "Integration of porous silicon chips in an electronic artificial nose", *Sensors and Actuators B*, 69 (2000) pp. 193-198.

Li, Yang Yang, et. al., "Polymer Replicas of Photonic Porous Silicon for Sensing and Drug Delivery Applications", *Science*, 299, 2042, (2003).

Lin, Victor S.-Y, et. al., "A Porous Silicon-Based Optical Interferometric Biosensor", *Science* 1997, 278, 840.

Link, Jamie R., et. al., "Smart dust: Self-assembling, self-orienting photonic crystals of porous Si", , *Proc. Nat. Acad. Sci*, 2003, 100, 10607.

Loni, A., "Capping of Porous Silicon", *Properties of Porous Silicon*, vol. 18, (e. L. Canahm) pp, 51-58, (Short Run Press Ltd., London), 1997.

Mazzoleni, C., et. al., "Application to optical components of dielectric porous silicon mutlilayers", *Appl. Phys. Lett.,* 67 (20) Nov. 13, 1995.

Meade, Shawn O., et. al. "Porous Silicon Photonic Crystals as Encoded Microcarriers", *Adv. Mater.* Oct. 18, 2004, 16, No. 20.

Navarro, M., et. al., "Improvement of the porous silicon sacrifical-layer etching for micromachining applications", *Sens. Actuators* A 1997, 62, 676.

Navarro, M., et. al., Electrochemical etching of porous silicon sacrifical layers for micromachining applications, Micromechanics *Microeng.* 1997, 7, 131.

Okuyama, K., et. al., "Preparation of nanoparticles via spray route", *Chem. Eng. Sci.* 2003, 58, 537.

Pavesi, L., et. al., "Random porous silicon multilayers: application to distributed Bragg reflectors and interferential Fabry-Perot filters", *Semicond. Sci. Technol.,* 12 (1997) pp. 570-575.

Pellegrini, Vittorio, et. al., "Enhanced optical properties in porous silicon microcavities", *Physical Review B*, vol. 52, No. 20, Nov. 15, 1995.

Ruminski, Anne, et al., "Humidity-Compensating Sensor for Volatile Organic Compounds Using Stacked Porous Silicon Photonic Crystals", *Adv. Funct Mater.*, 2008, 18.

Ruminski, Anne, et. al., "Internally Referenced Remote Sensors for HF and $Cl_2$ Using Reactive Porous Silicon Photonic Crystals", *Adv. Funct. Mater,* 2011, 21.

Salem, M.S., et. al., "Electrochemical preparation of a rugate filter in silicon and its deviation from the ideal structure", *J. Appl. Phys.*, 101, 063503 (2007).

Schmedake, Thomas, et. al, "Standoff Detection of Chemicals Using Porous Silicon "Smart Dust" Particles", *Adv. Mater.* 2002, 14, 1270.

Sirbuly, D.J., et. al., "Patterned Microstructures of Porous Silicon by Dry-Removal Soft Lithography", *Adv. Mater.* 2003, 15, 149.

Snow, P.A., et. al., "Vapor sensing using the optical properties of porous silicon Bragg mirrors", *Journal of Applied Physics*, Vo. 86, No. 4, Aug. 15, 1999.

Stewart, Michael P., "Photopatterned Hydrosilylation on Porous Silicon", *Angew. Chem. Int. Ed. Engl.* 1998, 37,3257.

Thonissen, M., et. al., "Multilayer structures of porous silicon", *Properties of Porous Silicon*, vol. 18, (e. L. Canahm) pp. 30-37, (Short Run Press Ltd., London) May 1997.

Vincent, G., "Optical properties of porous silicon superlattices", *Appl. Phys. Lett.,* 64 (18), May 2, 1994.

Zangooie, S., et. al., "Vapor sensitivity of thin porous silicon layers", *Sensor and Actuators B,* 43 (1997) pp. 168-174.

Zangooie, Shahin, et. al., "Infrared ellipsometry characterization of porous silicon Bragg reflectors", *Applied Optics*, vol. 40, No. 6 Feb. 20, 2001.

\* cited by examiner

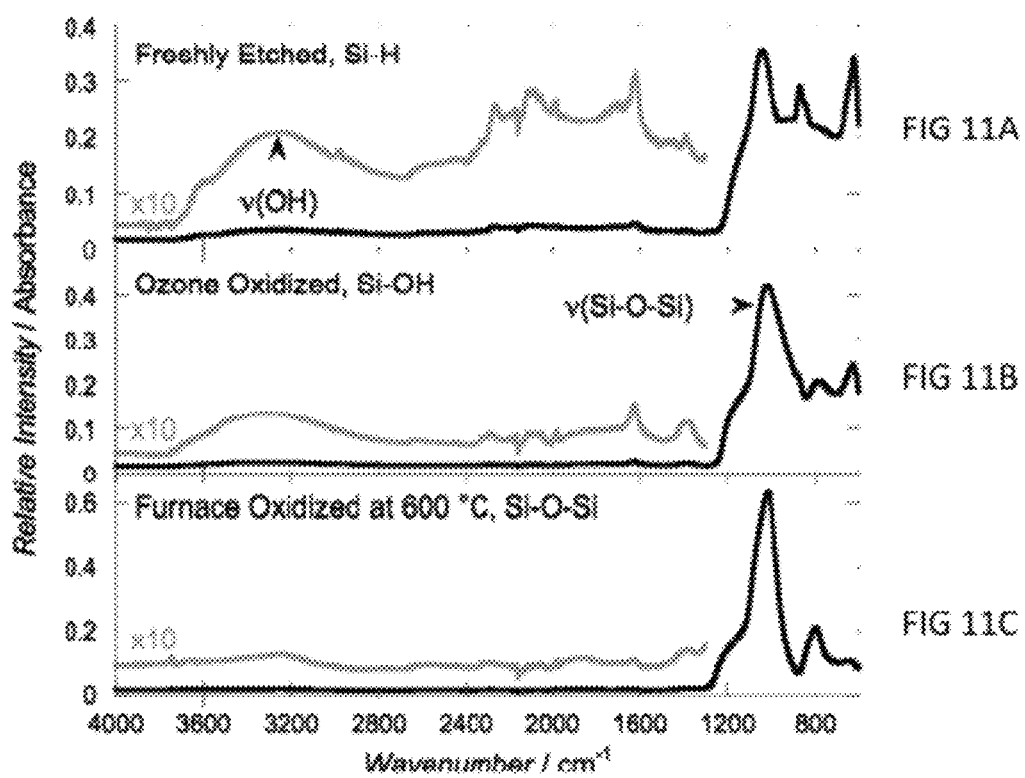

POROUS OPTICAL SENSOR WITH FIDUCIAL MARKER AND METHOD FOR DETECTION OF ANALYTES

PRIORITY CLAIM AND REFERENCE TO RELATED APPLICATION

The application claims priority under 35 U.S.C. §119 from prior provisional application Ser. No. 61/378,442, which was filed on Aug. 31, 2010, which is incorporated by reference herein.

STATEMENT OF GOVERNMENT INTEREST

This invention was made with government support under Grant No. DMR-0452579 awarded by the National Science Foundation. The government has certain rights in the invention.

FIELD

Fields of the invention include porous optical sensors and chemical sensing. Example applications of the invention include remote chemical sensing, point of care biosensing, water quality monitoring, and air quality monitoring.

BACKGROUND

Porous films are well-suited to chemical sensing, as the optical response of the films shifts in a predetermined manner. However, ambient conditions can cause drift over time. Humidity, in particular, affects the baseline optical signal from a porous film, such as porous silicon, which can interfere with the ability to detect an analyte of interest via optical methods. The base line signal of a porous silicon film can also drift over time as oxidation caused by exposure to air reduces the natural hydrophobicity of an etched porous silicon layer over time, increasing the response of a porous silicon sensor to water vapor. The oxidation reaction thus leads to significant zero point drift. Another problem with optical interrogation of porous films concerns off-angle measurements. This is particularly problematic in remote sensing, where the angle of sensing is difficult to guarantee and replicate. A porous film that is optically interrogated at different angles can produce different signals. The variance in signals caused by angular variance in interrogation also interferes with the ability to detect or identify analytes of interest.

Optical reflectance is the most commonly used method used to interrogate porous sensors, and provides a convenient transduction mechanism that can be probed at a distance, either in free space or at the distal end of an optical fiber for remote detection of chemicals. In a free-space optical configuration, the intensity of one or more wavelengths of light reflected from the porous Si-based photonic structure is monitored using a laser or incoherent light source. Reflected intensity depends on the refractive index of the porous matrix, which is related to its chemical composition. Any adsorbate or chemical reaction that alters the chemical composition can, in principle, be detected. However, problems arise with signal drift as discussed above. In addition, the need to detect a reflectance spectrum requires optical sensing equipment that limits application.

A double layer sensor has been used to compensate for humidity drift. Ruminski, Moore & Sailor, "Humidity-Compensating Sensor for Volatile Organic Compounds Using Stacked Porous Silicon Photonic Crystals," discloses double stack porous silicon sensors having a hydrophobic top stack and a hydrophilic bottom stack. The optical spectrum of the double-stack structure provides an effective structure to discriminate VOCs (volatile organic contaminants) from water vapor. Shifts in the peak frequencies from both photonic crystal stacks in the sensor are measured simultaneously. The hydrophilic and hydrophobic stacks respond differently to water and to VOC. The different response and the simultaneous measurement permits the effect of changing humidity to be nulled by calculating the weighted difference between the two peak frequencies. The method requires determination of a constant nulling factor for the double stack sensor.

Porous sensors can also be made chemically specific. Porous Si photonic crystals, for example, can be modified to incorporate a chemical reaction that is specific for an individual analyte or for a class of similar analytes. Oxidized porous Si is normally stable in air, but traces of $HF_{(g)}$ react with and remove the surface oxide, generating a blue shift in the reflectance spectrum. This reaction can be coupled to other reactions that produce HF, for example, the catalytic hydrolysis of fluorophosphonate nerve agents by copper-containing catalysts. Incorporation of a copper-based hydrolysis catalyst in a porous $SiO_2$ matrix generates a sensor that is specific for the P—F bonds of the nerve agent sarin and related fluorophosphonates. See, e.g., H. Sohn, S. Létant, M. J. Sailor, W. C. Trogler, J. Am. Chem. Soc. 122, 5399 (2000). Another surface chemistry that is selective for certain classes of chemicals is silicon hydride. The electrochemical preparation of porous Si generates a surface that is covered with Si—H, $SiH_2$, and $SiH_3$ species. Though kinetically stable in air, this surface is rapidly degraded in corrosive environments (e.g. $O_2$, $O_3$, $Cl_2$, $NO_x$). The reactions convert Si—Si and Si—H bonds to Si—O, which results in a decrease in refractive index of the porous Si matrix and a characteristic blue shift in the reflectance spectrum.

Detection of HF in environmental samples is commonly accomplished not with porous silicon but instead using a collection agent that is exposed for a prescribed period of time and subsequently subjected to a laboratory-based analysis. For example, filter paper impregnated with $K_2HPO_4$ can be used as a collection agent; after exposure the sample is eluted with 0.1 M sodium citrate and the fluoride concentration is determined potentiometrically. This method can detect HF gas in the concentration range 0.68-5.45 ppm, over a period of 48 h. Polymer-based collection agents have also been employed; an alkaline impregnated polypropylene film detects HF gas in the concentration range 0.1-387 ppm in 4 h when subjected to electrochemical analysis using a fluoride selective-ion electrode. These dosimeters are designed to respond to HF in the gas phase only, and cannot detect aqueous hydrofluoric acid. Also, the methods do not monitor HF in real-time, but must be analyzed after exposure.

A common problem with porous sensors in general and any of the specific porous sensors discussed above is the aforementioned humidity and off angle measurement problems. Either or both of these issues can result in significant errors associated with detection of chemicals of interest in the environment using photonic materials, specifically, zero point drift of the measured spectrum and dependence of the spectrum on the observer-sample angle.

SUMMARY OF THE INVENTION

The invention provides a porous sensor and sensing methods using a porous nanostructure having an optical response and having a portion of the porous nanostructure filled with a fiducial marker that is non-reactive to an analyte of interest. In preferred embodiments, a nonreactive polymer, such as inert polystyrene, serves as the fiducial marker, which acts as an internal spectral reference. The polymer fiducial marker protects that portion of the sensor from reaction with analytes, including corrosive analytes.

In a preferred sensing method, reflectance spectra from both the polymer-filled and reactive portions of the porous nanostructure are acquired simultaneously. The fiducial marker provides an internal reference that permits compensation for humidity as the fiducial marker is not affected by humidity. The fiducial marker also allows elimination of artifacts associated with shifts of the resonance peak that result from variance of the angle of incidence of an optical probe.

The sensor and sensing methods including the fiducial marker also permit analyte detection that is unaided by complex optical equipment. A change in color relative to the fiducial marker permits analyte detection by a human observer or simple optical sensing and discrimination techniques based upon contrast that do not require more complex spectral analysis.

A particular preferred sensor and sensing method of the invention provides for sensitive detection of HF. High-temperature air or room-temperature ozone oxidation reactions are used to prepare the HF-reactive surface, and it is found that the ozone oxidation reaction produces a more sensitive HF sensor. Such a sensor also preferably includes a fiducial sensor.

BRIEF DESCRIPTION OF THE DRAWINGS

FIGS. 11A-11C shows the ATR-FTIR spectrum of as-etched porous Si after exposure to chlorine for 30 min. displays Si—O and Si—OH bands characteristic of silicon oxide and of surface-adsorbed water, respectively.

DETAILED DESCRIPTION OF THE PREFERRED EMBODIMENTS

Figure 1:
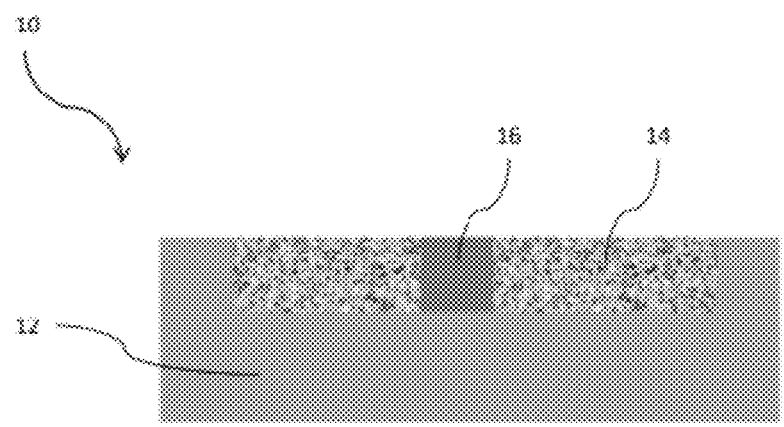
FIG. 1 shows a preferred sensor of the invention including a porous nanostructure and a fiducial marker.

Porous sensors and sensing methods of the invention incorporate a inert fiducial marker, preferably an inert polymer, as an internal standard to enable reliable detection of chemical or biological compounds. Preferred porous sensors are specific to particular compounds of interest except in the region of the fiducial marker that is substantially non-reactive and thereby provides a constant response that will not drift with changing humidity or in the presence of the analyte.

The incorporation of an internal standard into the sensor thus allows more reliable detection of chemical or biological compounds. A preferred sensor is formed of nanoporous material that is reactive towards a chemical or biological analyte(s) of interest, except in a portion of a fiducial marker. In the fiducial marker portion, the pores include a substance that is not reactive towards the intended chemical or biological analyte. The fiducial marker substance should also be selected to be substantially insensitive to environmental conditions that can adversely affect sensing. In preferred embodiments, the fiducial marker substance can be an organic polymer or polymer blend, a biopolymer or biopolymer blend, an organic compound or compounds, an inorganic compound or compounds, or a mixture of more than one of the above compounds.

Example preferred sensor material is porous silicon. Additional preferred embodiments include other porous semiconductors and insulators. A preferred silicon photonic crystal structure is anodically etched $p^{++}$ type, B-doped, (100)-oriented crystalline silicon wafers in a solution of aqueous HF:ethanol. Exemplary etch parameters for an example rugate structure involve a sinusoidal current waveform oscillating between 10 and 35 $mA/cm^2$ with 100 repeats and a periodicity of 10 s. Many variations of porous structures can be realized with different etching conditions, and many chemical and biological sensitivities can be created. Information for etching conditions and sensing affinities can be found, for example, in Sailor et al U.S. Pat. Nos. 7,042,570; 7,713,778; 7,443,811; 7,942,989; 7,318,903; 7,903,239; 7,759,129; and 7,889,954; and in Sailor et al U.S. Published Application Nos. 2005-0042764; 2006-0105043; 2007-0148695; 2007-0051815; 2007-0108465; and 2008-0296255. Such alternative etching conditions and sensing affinities as well as others that are known in the art can be used in preferred embodiment sensors of the invention that include a fiducial marker.

Preferred methods of fabrication form a sensor that is specific to an analyte of interest and that includes a fiducial marker and detection methods. In one embodiment a porous material is prepared to display an optical reflectivity spectrum that can be monitored using an optical reflectance spectrometer or by visual inspection. The porous material is treated to be specifically reactive toward a chemical or biological analyte of interest. Pores are filled in a marker area with a fiducial marker substance (e.g., an organic polymer) that is not reactive towards the intended chemical or biological analyte. In a method of sensing, the analyte is detected via instrumental or visual observation of a difference in spectral reflectivity or color between the chemically nonresponsive fiducial reference and the rest of the porous material. The fiducial marker method eliminates artifacts associated with varying angle of incidence of an optical probing detector relative to a one-dimensional photonic crystal sensor that lacks a fiducial marker. When a sensor of the invention is probed at an angle, the fiducial marker reflectivity peak wavelength shifts by the same nm amount as the reactive porous Si reflectivity peak. This permits a comparison between the wavelength position of both signals before and after a sensing event to eliminate errors in signal response resulting from changes in probing angle.

The porous sensor is preferably treated to provide specific reactivity toward an analyte of interest. For example, to achieve class specificity for chloramines, a reactive surface hydride or mixed surface hydride/alkane can be fabricated. These surfaces react with oxidants to produce a spectral blue-shift. A portion of the porous sensor is infused with an inert polymer that serves as a fiducial marker for the reaction, enabling a determination of chloramine contamination by direct visual comparison either by human observation or by simple optical electronic equipment and analysis. The spectrum of the porous Si material containing the inert polymer fiducial marker does not shift, or does not shift substantially compared to other portions of the sensor, upon exposure to chloramines. In addition to simple detection of analyte, such as chloramine, relative spectral shifts can be measured and correlated with chloramine concentration.

Experiments have demonstrated that the invention provides for accurate detection of HF acid as an example analyte. High-temperature air or room-temperature ozone oxidation reactions are used to prepare the HF-reactive surface, and it is found that the ozone oxidation reaction produces a more sensitive HF sensor. A porous sensor, in another example, is treated to exhibit specific reactivity for HF, by formation of a reactive surface oxide on the sensor. The reactive oxide surface is also stable in air, but it produces a spectral blue-shift in the presence of HF(g). A portion of the porous sensor is infused with an inert polymer that serves as a fiducial marker for the reaction, enabling a determination of HF contamination by direct visual comparison either by human observation or by simple optical electronic equipment and analysis. Relative spectral shifts be measured and correlated with HF concentration.

As another example treatment for specific reactivity to ozone, freshly etched porous silicon surfaces (H-terminated) can be optimized to respond to ozone. High-temperature air or room-temperature ozone oxidation reactions can be used to prepare the HF-reactive surface, and experiments have shown the ozone oxidation reaction produces greater sensitivity to HF (LLOD of 0.1% HF in water). Generally, treatments are selected according to analytes of interest.

Sensors of the invention and sensing methods can also be used, for example, as a protease sensor with appropriate treatment. Artisans will appreciate broader aspects of the invention from the following discussion of experiments and specific embodiments.

Referring now to FIG. 1, a porous nanostructure sensor 10 of the invention is shown. The sensor 10 is formed in a substrate 12 and includes a nanoporous sensor region 14. The sensor includes a fiducial marker 16 in a reference region and remaining portions of the nanoporous sensor region 14 accept analyte into the pores. In preferred embodiments, a nonreactive polymer, such as inert polystyrene, serves as the fiducial marker 16, which acts as an internal spectral reference. The polymer fiducial protects that portion of the sensor from reaction with analytes, including corrosive analytes. The fiducial marker fills the pores in that region and provides a constant optical reference, which is useful as a spectral reference in reflectance measurements, or in simple visual observations. The remaining portions of the nanoporous sensor regions are preferably prepared to be specific to an analyte of interest.

During sensing, the fiducial marker 16 provides an internal reference that can correct for signal drift and artifacts resulting from off axis measurement. The wavelength of a reflectance peak decreases at probing angles off of normal incidence. This property adds an extra variable that must be considered when analyzing sensor response. The angular dependence is particularly problematic in a remote sensing configuration, where the angle between the light source and the face of the porous sensor chip 10 cannot necessarily be fixed. The fiducial marker 16 provides a second reflectance peak that can be used to correct for angular fluctuations. In addition, the fiducial marker provides a distinct visual reference that can be used for simple detection of analytes that don't require spectral analysis of a reflectance spectrum from the sensor. Introduction of an analyte will introduce color change in the nanoporous sensor region 14 but not the region of the fiducial marker. This color change can be observed by a human observer or by simply optical detection techniques.

Experiments were conducted with porous silicon sensors including polymer fiducial markers. In the experiments, porous sensing regions were made specific to analytes of interest. Two reactive surface chemistries, silicon oxide and silicon hydride, to detect HF and $Cl_2$, respectively, were used as benchmarks in experiments. The experiments demonstrate additional features of the invention.

Experimental Data

Porous silicon photonic crystals were prepared by electrochemically etching boron-doped $p^{++}$-type crystalline silicon in a solution of aqueous hydrofluoric acid and ethanol. The doped silicon wafers were Single-crystalline highly doped p-type Si (0.0008-0.0012 Ω-cm resistivity, (100) polished, B-doped) was purchased from Siltronix Corp. The etching solution was Aqueous HF (49%), hydrochloric acid, methanol and hexane were purchased from VWR International. Polystyrene (MW=45,000 Da) was purchased from Aldrich, ethanol from Rossville Gold Shield Chemical Company, and oxygen from Westair Gases & Equipment.

A computer-controlled sinusoidal current density waveform was applied to the silicon anode, resulting in a multi-layered porous Si film containing a pseudo-sinusoidal porosity gradient. The reflectance spectrum of the resulting material approximates a Rugate filter, displaying a peak corresponding to the stop band of the photonic crystal. The wavelength of the reflectance peak is controlled by the period and average value of the current density used in the electrochemical etch. Specifically, porous Si photonic crystals containing a single spectral reflectance peak were formed by anodization of highly doped p-type silicon wafers in a 3:1 v:v solution of aqueous hydrofluoric acid:ethanol in a two-electrode configuration using a platinum ring counter-electrode. Etching was performed in a Teflon etching cell using a galvanostat (Princeton Applied Research Model 363) under computer control (LabVIEW, National Instruments). The hydrofluoric acid solution was mixed during the etching process to minimize hydrogen bubble formation on the sample surface and to encourage etchant solution exchange. For the rugate samples, a cosine current density waveform varying between 13.3 and 39.8 mA/cm$^2$ with a period of 12 s and 100 repeats was used to etch the porous layer. For gravimetric analysis, samples were etched at a constant current density of either 13.3 or 39.8 mA/cm$^2$ for 10 min. Samples were etched on the polished side of the silicon wafer except for samples whose reflectivity spectra were probed at an incident angle of 40°—these samples were etched on the non-polished side.

As-etched samples ("Si—H") were used without further processing for the $Cl_2$-reactive sensor experiments. HF-reactive sensors were prepared by oxidation. Two types of oxide-terminated surfaces were prepared: a thermal oxide prepared by oxidation in air at 600° C. for 90 min, and an ozone-derived oxide prepared by exposure to ozone from a plasma source. Ozone-oxidized samples ("Si—OH") were prepared by placing as-etched, H-terminated porous Si samples in a flowing stream of ozone (Ozone Solutions, product ID OZV-8, flux of 8 g h$^{-1}$) for 4 min., followed by heating at 180° C. for 30 min to partially dehydrate the oxide. Thermally oxidized samples ("Si—O—Si") were prepared by etching silicon with a cosine waveform of the same current density minimum and maximum, but to with a period of 14 sec. and 86 repeats. Samples were then inserted into a tube furnace (Lindberg/Blue M) under air at 600° C. for 90 min.

A fiducial marker consisting of polystyrene was added by pipeting a solution of polystyrene in toluene (1 µL, 12% by mass) onto the porous film prior to heating in an oven at 180° C. for 30 min experimental data and the calculations show that porosity decreases upon oxidation, consistent with the volume expansion of the pore walls that can be expected when the silicon surface is converted to silicon oxide. The calculated volume percentages of silicon dioxide for rugate samples are in good agreement with the results obtained on constant current-etched samples: 6.9%±0.3% after ozone oxidation for 4 min.; 11.7%±1.7% after thermal treatment at 180° C. for 30 min. of ozone-oxidized samples; and 40.3%±0.6% for samples thermally oxidized at 600° C. for 90 min.

TABLE 1

Measured and Calculated Porosity and Thickness of Porous Si

| Sample chemistry | Current density etching profile[a] | Thickness (µm) SEM[b] | Calculated[c] | Average porosity (%) Gravimetric[d] | Calculated[c] |
|---|---|---|---|---|---|
| Si—H (as-etched) | 13.3 mA cm$^{-2}$ | 4.7 ± 0.1 | 4.3 ± 0.1 | 61 ± 1 | 57.6 ± 0.1 |
|  | 39.8 mA cm$^{-2}$ | 13.6 ± 0.2 | 12.7 ± 0.1 | 67.8 ± 0.5 | 60.8± 0.6 |
|  | Rugate | 17.7 ± 0.2 | 15.9 ± 0.1 | 67.5 ± 0.6 | 58.8 ± 0.1 |
| Si—OH (ozone oxidized) | 13.3 mA cm$^{-2}$ | 4.59 ± 0.08 | 4.2 ± 0.6 | 51 ± 2 | 50.2 ± 0.6 |
|  | 39.8 mA cm$^{-2}$ | 13.6 ± 0.4 | 12.2 ± 0.2 | 59.3 ± 0.6 | 53.4 ± 0.2 |
|  | Rugate | 18.3 ± 0.3 | 15.9 ± 0.2 | 59 ± 1 | 51 ± 1 |
| Si—O—Si (furnace oxidized) | 13.3 mA cm$^{-2}$ | 4.57 ± 0.07 | 4.0 ± 0.1 | 37 ± 3 | 35.7 ± 0.3 |
|  | 39.8 mA cm$^{-2}$ | 14.0 ± 0.3 | 11.9 ± 0.2 | 49.6 ± 0.7 | 40.7 ± 0.4 |
|  | rugate | 18.7 ± 0.1 | 15.5 ± 0.2 | 48 ± 1 | 37.6 ± 0.3 |

[a]Rows designated "rugate" are cosine waveform, minimum and maximum current 13.3 and 39.8 mA · cm$^{-2}$, respectively, temporal period 12 s, 100 repeats for Si—H and Si—OH samples, temporal period 14 s, 86 repeats for Si—O—Si samples.
[b]Cross-sectional SEM measurement of cleaved samples. Errors represent 1 standard deviation of 3 measurements.
[c]From calculated spectral fit, as described in section 2.4. Errors represent 1 standard deviation of 3 measurements.
[d]Gravimetric measurement. As-etched and ozone oxidized porosities were calculated differently than furnace oxidized samples. See experimental section for details. Errors represent 1 standard deviation of 4-5 measurements.

Figure 2:
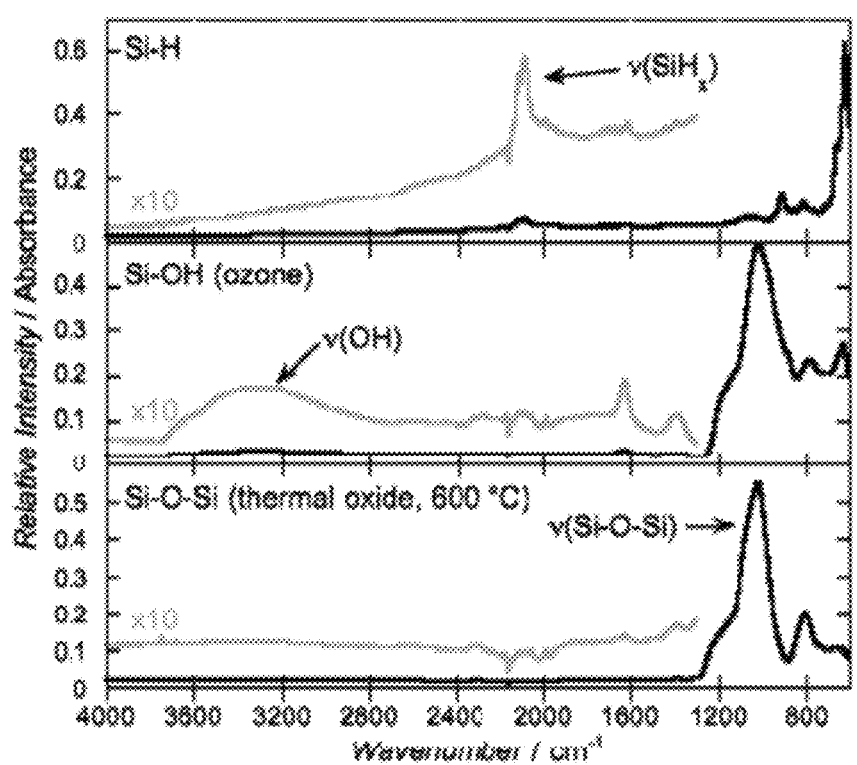
FIG. 2 shows ATR-FTIR spectra of porous Si samples prepared in experiments before and after oxidation.

Surface chemistry was characterized by attenuated total reflectance Fourier transform infrared (ATR-FTIR) spectroscopy. FIG. 2 shows ATR-FTIR spectra of porous Si samples before and after oxidation. The as-etched material ("Si—H") is predominantly covered with silicon hydride species. Ozone oxidation ("Si—OH") produces a more hydrophilic, hydroxylated surface, whereas thermal oxidation ("Si—O—Si") generates a dehydrated silicon oxide. The black traces represent full-scale spectra, and the portion of the spectrum shown in gray (>1300 cm$^{-1}$) is multiplied by 10 and offset along the y-axis for clarity. For both oxidation methods, sample spectra display strong bands associated with Si—O vibrations (1020 cm$^{-1}$). The ozone-oxidized samples also display a prominent band at 3300 cm$^{-1}$ assigned to OH stretching vibrations.

The thickness of the porous silicon layer was determined by cross-sectional scanning electron microscopy (SEM), and the results are presented in Table 1. Gravimetric analysis was used to measure porosity of the etched films (Table 1). Three types of etches were used to characterize the properties of each surface chemistry type: samples etched with a cosine current waveform, samples etched for 10 min at a constant current representing the minimum current density of the cosine waveform, and samples etched for 10 min at a constant current representing the highest current density of the waveform. Porosity of the as-etched rugate structures decreases upon oxidation, because oxidation causes a volume expansion that effectively reduces the diameter of the pores.

Results obtained for both ozone-oxidized and thermally oxidized rugate samples are reported in Table 1. As expected, the average porosity value of oxidized rugate samples falls between the porosity values of the two samples prepared at the lower and upper constant current values. Again, both the A portion of the porous matrices prepared in experiments were filled with an inert material fiducial material, polystyrene, to provide a chemically stable optical signature that could serve as a reference for the reactive chemical sensor. Polystyrene readily infiltrates the porous Si samples and it is substantially unreactive with HF. The fiducial marker optical reference was infused into a portion of the ozone-oxidized sample by spotting a small area of the surface with a solution of polystyrene in toluene, followed by 30 min of heating at 180° C. to remove the toluene solvent and to fully infiltrate the depth of the pores with polystyrene. Reflectance spectra obtained from the resulting samples display two distinct peaks, at 600 and 700 nm, corresponding to the stop bands of the air-filled and polystyrene-filled regions of the porous rugate filter, respectively.

Figure 3:
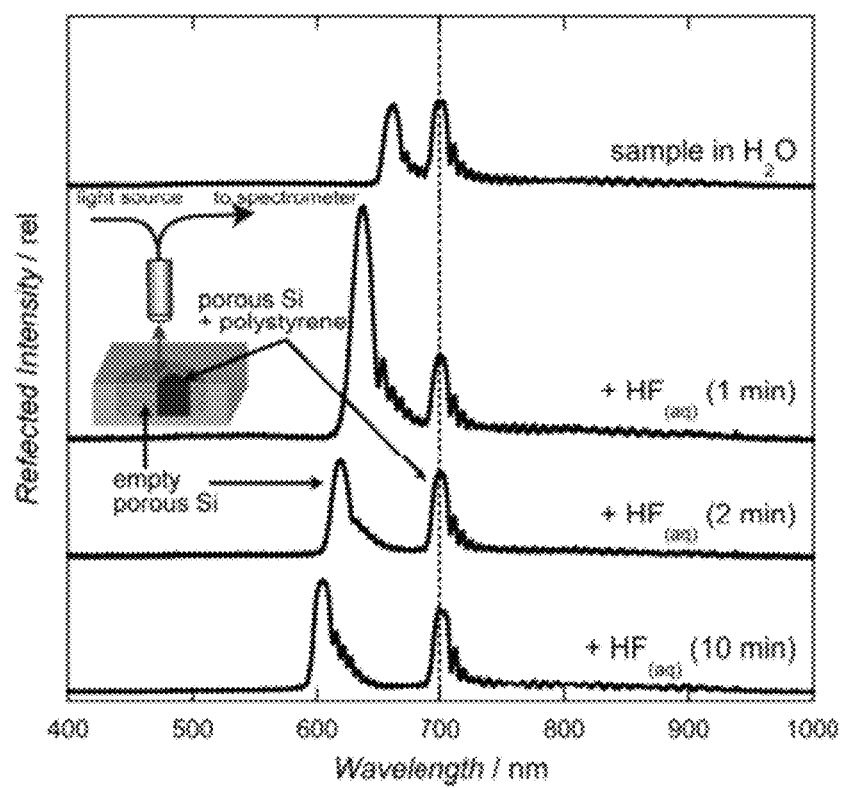
FIG. 3 shows the reflectance spectra of an ozone-oxidized porous Si sample containing a polystyrene fiducial marker, before and during exposure to aqueous HF (1.5%)

Immersion of the sample in water shifts the position of the 600 nm peak (corresponding to the air-filled region of the film) to 650 nm, as seen in FIG. 3, while the peak corresponding to the polymer-filled region shows no significant spectral shift. FIG. 3 shows the reflectance spectra of an ozone-oxidized porous Si sample containing an impregnated polystyrene fiducial marker, before and during exposure to aqueous HF (1.5%). The spectrometer optics encompassed both the polymer-filled and the unfilled regions of the film equally, spectra were acquired at the ozone oxidized porous silicon/polystyrene infused porous silicon interface. A cross-sectional schematic of the structure containing the polystyrene fiducial marker is shown in the inset. From top to bottom: reflectance peak of sample in deionized water, after 1 min., 2 min., and 10 min. exposure to 1.5% HF. Spectra were obtained on samples submerged in either water or 1.5% aqueous HF. As seen in FIG. 3, the fiducial marker provides a constant reference peak that is near 700 nm. The separation between the constant reference peak and the peak attributable to the HF infiltration into reactive portions of the sensor provides a powerful means for determination of HF and that is insensitive to probe angle variation and changing humidity.

The HF reaction mechanism in the reactive portion of the porous silicon sensor is of interest. Exposure of an ozone-oxidized porous Si photonic crystal to an aqueous hydrofluoric acid solution results in removal of the surface oxide via Eq. (1):

$$SiO_2 + 6HF \rightarrow Si_6^{2-} + 2H^+ + 2H_2O \qquad (1)$$

As the oxide is removed, the net refractive index of the film decreases, resulting in a blue shift of the photonic resonance. The solution does not attack polystyrene-filled porous Si, and the reflectance spectrum from this region of the film does not change. FIG. 3 shows the evolution of the reflectance spectrum, obtained with the optical probe beam overlapping both polymer-filled and unfilled regions of the chip, showing how the resonance from the polymer-filled photonic crystal can act as an internal standard, or fiducial marker, for the sensor. The intensity of the stop band peak associated with the open, actively dissolving region of the porous Si chip increases during the initial stages of dissolution. The intensity of the stop band depends on the index contrast between the repeating layers of the photonic crystal; the intensity increase observed in the early stages of dissolution indicates that the index contrast is increasing, presumably associated with the dissolution process. This effect might be attributable to the removal of silicon oxide or the generation of gas bubbles within the pore structure as the material dissolves.

Figure 4:
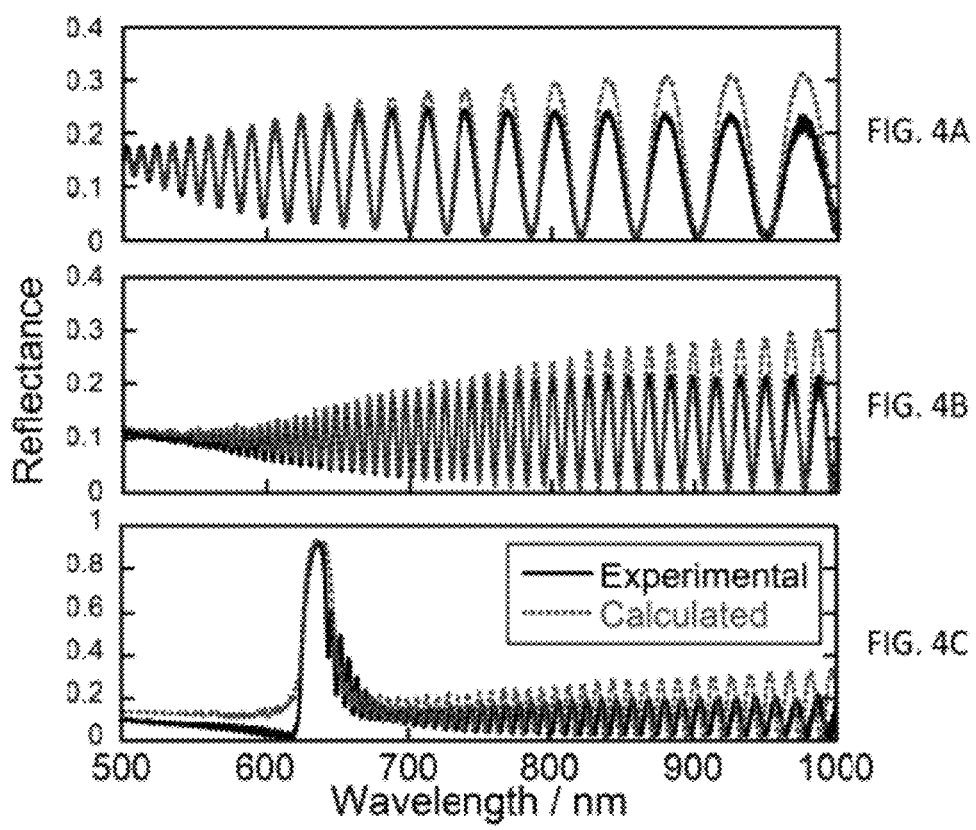
FIGS. 4A-4C shows reflectance spectra of porous Si samples etched using constant and cosine-modulated current.

Theoretical calculations of the reflectance spectra of porous Si containing the polystyrene fiducial markers were performed to verify the sample parameters of thickness and porosity, to predict the response of the samples to HF exposure, and to interpret the angular dependence of the reflectance spectra. Optical reflectance spectra were fit to numerical calculations that incorporated the wavelength dependent refractive index of silicon, the Bruggeman effective medium model, and the optics equations describing the various structures used in the experiments. Reflectance spectra were acquired in the range 500 to 1000 nm for all sample types (constant current etch, rugate etch, freshly etched, thermal and ozone oxidized, with and without polymer fiducial marker). Typical reflectance spectra of porous Si samples etched using constant and cosine-modulated current are presented in FIG. 4. FIGS. 4A-4C include experimental and calculated reflectance spectra of as-anodized samples etched with constant current density of 13.3 mA/cm² for 10 min. (FIG. 4A), 39.8 mA/cm² for 10 min. (FIG. 4B), and with a cosine modulated current (FIG. 4C). The cosine function was bounded by a maximum current density of 39.8 mA/cm² and a minimum current density of 13.3 mA/cm²

Samples etched at a constant current contain a uniform porous layer that acts as a Fabry-Perot cavity; the optical reflectance spectra display a series of fringes corresponding to constructive and destructive interference. The samples etched with a sinusoidal current density waveform display a strong resonance peak in the reflectance spectrum that corresponds to the stop band of the photonic crystal (rugate filter). The spectra depend on the physical morphology and optical properties of the porous Si layers: thickness and refractive index for constant-current etched samples; modulation period and refractive index for sinusoidal-current etched samples. Oxidation treatments as well as infiltration of the porous matrix with solvent or polymer produce predictable changes in the Fabry-Perot fringes and the rugate peak position that were quantitatively fit to the theoretical curves.

Porosity and thickness of as-etched (Si—H) samples etched for 10 min. with a constant current density (13.3 mA/cm² or 39.8 mA/cm²), were calculated using data obtained from reflectance spectra acquired in air. Additionally, reflectance spectra collected with different media filling the porous layer provide information that can yield the properties of thickness and porosity for a given porous Si sample. Infiltration of a liquid into the porous structure leads to predictable changes in the position of the reflectance peaks (typically a red shift relative to air). This approach is referred to as SLIM, for Spectroscopic Liquid Infiltration Method. Calculations of the reflectance spectrum of air and liquid-infiltrated samples yield results that agree well with the gravimetric and SEM measurements for thickness and porosity reported in Table 1. A difference of a few percent between theoretical and measured values is observed, which is attributed to inaccuracies of the gravimetric, SEM, and optical measurements and the calculations employed. For instance, the gravimetric measurement is a destructive method that determines the average porosity of the entire film, whereas the optical measurement is determined from the reflectance spectrum originating from a single (mm-diameter) spot on the sample. Thus, variations in thickness or porosity in the x-y plane of the sample are not accounted for with the optical fitting method.

The samples used in the experiments contain two or more components: silicon, silicon oxide, air, a liquid, or the polymer fiducial. In order to calculate the porosity and thickness from the experimental reflectance spectra, an appropriate effective medium model must be employed. The Bruggemann approximation was used for this purpose. For a medium containing two distinct components the relationship is given by Eq. 2:

$$(1 - V_{Si}) \frac{n_{fm}^2 - n_{ps}^2}{n_{fm}^2 + 2n_{ps}^2} + V_{Si} \frac{n_{Si}^2 - n_{ps}^2}{n_{Si}^2 + 2n_{ps}^2} = 0 \qquad (2)$$

where $V_{Si}$ is the volume fraction of silicon in the porous matrix, $n_{fm}$ is the refractive index of the medium filling the pores (air, liquid, or polymer in this work, assumed to be wavelength-independent), $n_{Si}$ is the wavelength-dependent refractive index of the crystalline silicon, and $n_{ps}$ is the wavelength-dependent refractive index of the composite porous Si layer, incorporating both components. The Bruggemann effective-medium approximation has been demonstrated to yield results in good agreement with experimental measurements when applied to porous Si constructed from highly doped p-type wafers. Solution of Eq. 2 for a given porosity value $P=1-V_{Si}$ yields a wavelength-dependent value for the porous silicon refractive index $n_{ps}(\lambda, P)$, which is in good agreement with experimental measurements. In the calculations discussed herein, it was assumed that the medium inside the pores completely fills the pore volume. This assumption is supported by the close match observed between the calculated and experimentally determined reflectance spectrum, porosity, and thickness.

Oxidation of the porous Si samples introduces a third component into the medium, which was modeled using the three-component Bruggemann approximation:

$$\left( V_{Si} - \frac{V_{ox}}{2.27} \right) \frac{n_{Si}^2 - n_{ps}^2}{n_{Si}^2 + 2n_{ps}^2} + \qquad (3)$$

$$V_{ox}\frac{n_{ox}^2 - n_{ps}^2}{n_{ox}^2 + 2n_{ps}^2} + \left(1 - V_{Si} - \frac{1.27}{2.27}V_{ox}\right)\frac{n_{fm}^2 - n_{ps}^2}{n_{fm}^2 + 2n_{ps}^2} = 0$$

where $V_{ox}$ is the fraction volume of the oxide, and $n_{ox}$ is the wavelength-dependent refractive index of silicon dioxide. Oxidation of the internal pore surface is assumed to occur uniformly throughout the entire film thickness. To be consistent with Eq. 2, here $V_{Si}$; is defined as the volume of silicon that was present in the porous Si matrix prior to oxidation. Reaction of silicon with oxygen produces a 2.27-fold volume increase in the silicon skeleton. Assuming that the volume fraction of silicon oxide is $V_{ox}$, the volume fraction of silicon is reduced by $V_{ox}/2.27$ and the void volume fraction is $(1.27/2.27)V_{ox}$, relative to as-etched samples. For oxidized samples, the porosity depends on the fraction of silicon in the porous matrix before oxidation ($V_{Si}$), the as-etched porosity ($P=1-V_{Si}$), and the volume fraction of silicon dioxide present after oxidation ($V_{Ox}$). Once the initial porosity $P=1-V_{Si}$; is known, a wavelength-dependent value for the refractive index of the oxidized porous Si sample, $n_{ps}(\lambda, P, V_{ox})$, can be obtained by solving Eq. 3 for a given oxide volume. Results of calculations on samples etched at a constant current density of 13.3 mA/cm$^2$ or 39.8 mA/cm$^2$ and subjected to ozone and thermal oxidation are reported in Table 1.

Consistent with the gravimetric measurements, the calculations show that both the thermal and the ozone oxidation treatments lead to a reduction in porosity. Thermally oxidized samples display the larger reduction in porosity, as expected due to the more extensive degree of oxidation. The calculations also provide the volume fraction of silicon dioxide in the porous matrix. Ozone oxidation yields a volume fraction of 7.1%±0.2%. Thermal dehydration of this sample (180° C. for 30 min) increases the volume fraction to 10.2%±0.7%. Samples thermally oxidized at 600° C. (for 90 min) show a significantly larger degree of oxidation; the volume fraction in this case is 38.6%±0.7%. Oxidation of samples produces a shift of the reflectance spectrum (blue shift) with respect to as-etched samples, due to the reduction of the effective refractive index of the material upon conversion of a portion of the silicon skeleton to silicon dioxide.

The refractive index profile of porous Si photonic crystal samples etched with a cosine current density waveform (so-called rugate filters) can be represented as:

$$n(x) = n_{av} + \frac{\Delta n}{2}\sin\left(\frac{4\pi n_{av} x}{\lambda_0}\right) = n_{av} + \frac{\Delta n}{2}\sin\left(\frac{2\pi x}{p}\right) \quad (4)$$

where $n_{av}$ is the average refractive index of the sample, $\Delta n$ is the refractive index contrast (peak-to-peak variation), $\lambda_0$ is the resonance peak wavelength, x is the direction perpendicular to the wafer surface along which the index modulation holds, and p is the spatial period of the index modulation. From Eq. 4 the relationship between the average value of refractive index, stop band peak wavelength, and spatial modulation period can be obtained:

$$\lambda_0 = 2n_{av}(\lambda_0, P_{av})p \quad (5)$$

where the dependence of the refractive index on wavelength and on the average porosity $P_{av}$, are explicitly indicated. Once the value of the stop band peak $\lambda_0$ is determined from the experimental reflectance spectrum, Eq. 5 provides a non-linear equation linking average porosity and spatial period of the photonic crystal, which are the two unknowns. Infiltration of a liquid (or polymer) into the porous matrix leads to predictable changes in the position of the resonance peak (red shift), so that an additional equation is obtained when the pores contain a medium other than air. Since neither the average porosity nor the spatial period of the rugate filter change with liquid infiltration, the ratio between the two versions of Eq. 5 (representing the same sample containing two different filling media) yields an equation that depends only on the average porosity of the rugate, through the average refractive index of the porous layer:

$$\frac{\lambda_0}{\lambda_1} = \frac{n_{av}(\lambda_0, P_{av})}{n_{av}(\lambda_1, P_{av})} \quad (6)$$

where the terms $\lambda_0$ and $\lambda_1$ correspond to wavelengths of the stop band resonances from a sample containing different filling media. The average refractive index of porous Si is a strictly monotonic function, both versus porosity (for a given wavelength) and versus wavelength (for a given porosity), at least in the range of wavelengths investigated in this work. Moreover, the ratio $$\frac{n_{av}(\lambda_0, P_{av})}{n_{av}(\lambda_1, P_{av})}$$

is expected to be a monotonic function of porosity for any wavelength value. This ensures that Eq. 6 can be numerically solved to find a unique solution for the sample porosity. Reflectance spectra of as-etched photonic crystals collected in air and after infiltration of the porous layer with a different liquid medium (methanol, ethanol and hexane) were then used to obtain an over-determined equation system, and thus a more precise solution by least-squares fit. Once the average porosity is calculated, the spatial period of the rugate can be obtained via Eq. 5.

For as-etched rugate samples, in air or after infiltration of the pores with liquid, the value of the refractive index to be employed in Eq. 6 was calculated using the two-component Bruggemann approximation of Eq. 2. Calculated results for rugate samples are also presented in Table 1, and they are in agreement with the porosity results on the single layer films. As expected, the average porosity of the rugate samples is midway between the porosity values found for samples etched at constant current density, using the minimum and maximum current values that were employed in the current waveform that etched the rugate samples. Comparison between the experimental and calculated results shows reasonable agreement, with a difference of a few percent both for thickness (SEM measurement) and porosity (gravimetry). In all cases, the calculated thickness and porosity values tend to under-estimate the experimentally determined ones.

Eqs. 5 and 6 were also used to obtain information on the porosity of rugate samples subjected to oxidation treatments. As observed with the samples etched under constant current conditions, oxidation of photonic crystals produces a blue shift of the resonance peak with respect to as-etched samples. Application of Eqs. 5 and 6 to the reflectance spectrum of an oxidized sample yields additional equations that can be combined with the equations pertaining to the sample prior to oxidation, yielding information on the volume fraction of oxide grown and, in turn, on the porosity of the oxidized sample. The refractive index value employed in Eqs. 5 and 6 was determined using the three-component Bruggemann approximation, according to Eq. 3.

Theoretical reflectance spectra of both constant current etched and rugate etched porous Si samples were calculated using a program written in the Matlab™ computer language that implements the characteristic matrix method. All parameters required for spectral calculation, i.e., thickness, as-etched porosity, porosity contrast, and silicon dioxide volume fraction, were obtained from experimental reflectance spectra via the methods discussed above. The porosity contrast value, needed to calculate rugate spectra, was obtained from the porosity of the two samples etched at constant current, representative of the maximum and minimum porosity limits in a rugate filter. The wavelength-dependent refractive index of silicon was used. Two- and three-component Bruggemann approximations were used to calculate the wavelength-dependent refractive index of porous silicon for a given porosity value, according to the methods described above. Optical absorption was not taken into account, due to the small value of the adsorption coefficient of silicon in the wavelength range investigated. Losses due to light scattering from the samples were also not considered.

The continuous variation of the refractive index of rugate samples was represented with a large number of discrete layers—30 per period of the refractive index profile. This number of layers is sufficiently large that the calculated reflectance spectrum does not change with addition of more layers. In all cases the calculated spectra were found to be in good agreement with the measured spectra, in terms of peak position and resonance full width at half-maximum (FWHM). The calculated reflectance spectra are also presented in FIGS. 4A-4C, superimposed on the experimentally determined spectra.

Porous Si multilayers (rugates) oxidized either by furnace (Si—O—Si) or ozone (Si—OH) oxidation were exposed to aqueous hydrofluoric acid solutions at concentrations of 13, 6.8, 3.4, 1.7, 0.86, 0.46, 0.23 and 0.11% HF by mass (140000, 69000, 34000, 17000, 8600, 4600, 2300 and 1100 ppm, respectively). Hydride-terminated (Si—H) samples were exposed under the same conditions for comparison. Initial reflectance spectra were acquired from samples submerged in deionized water for 3 min. The water was removed and the samples dried under a stream of dry $N_2$ prior to immersion in the HF solution of interest. Measured shifts of the reflectance peak maxima after 10 min. of exposure to aqueous HF solutions at the indicated concentrations are presented in FIG. 5.

Figure 5:
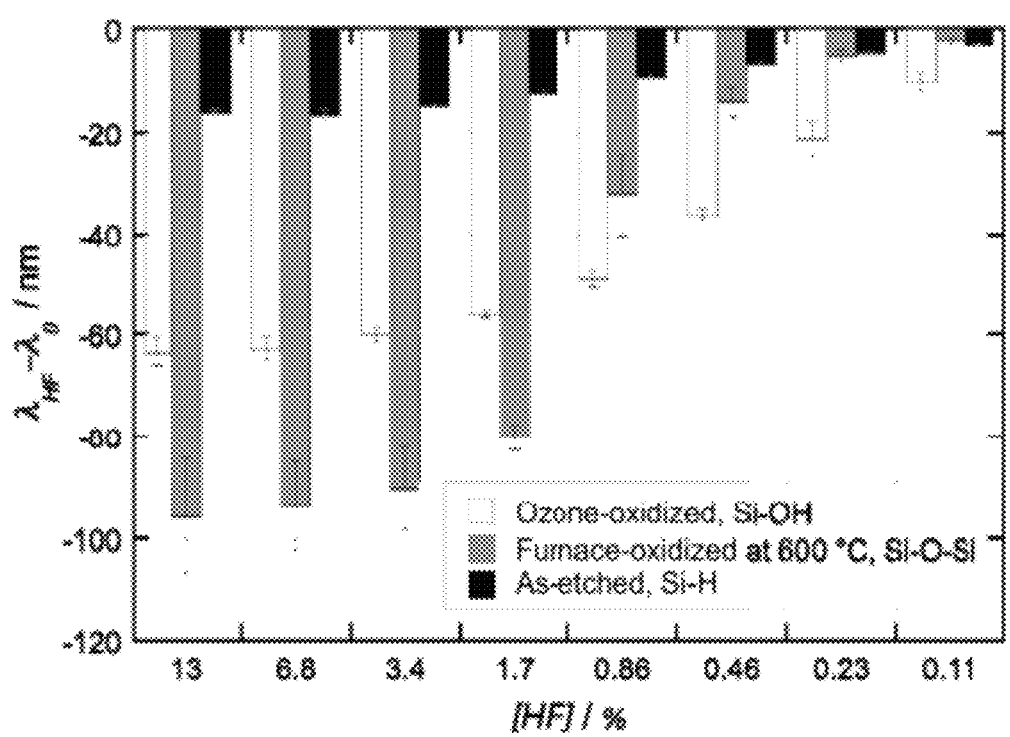
FIG. 5 shows the shift in reflectance peak maximum from ozone oxidized, furnace oxidized, and freshly etched porous Si rugate filters after 10 min. exposure to the indicated concentrations of HF in water.

FIG. 5 shows the shift in reflectance peak maximum from porous Si rugate filters after 10 min. exposure to the indicated concentrations of HF in water. The quantity ($\lambda_{HF}-\lambda_0$) is defined as the wavelength of the reflectance peak maximum measured immediately before introduction of $HF_{(aq)}$ ($\lambda_0$) subtracted from the wavelength of the reflectance peak maximum measured 10 min. after introduction of $HF_{(aq)}$ at the indicated concentrations ($\lambda_{HF}$). Negative values indicate a spectral blue shift. Three sample types are presented: ozone-oxidized (white bar), furnace-oxidized at 600° C. (gray bar) and as-etched, hydride-terminated porous Si (black bar). Data represent averages from 5 samples, with error bars representing 1 standard deviation For HF concentrations>1.7%, furnace-oxidized samples (Si—O—Si) display the largest change in reflectance peak wavelength of the 3 surface chemistry types studied, whereas at HF concentrations<1.7% ozone-oxidized (Si—OH) samples display the largest change. The dynamic range of the HF response for ozone-oxidized samples is slightly larger than that of the furnace-oxidized samples. The greater sensitivity of the Si—OH surface to low concentrations of HF corresponds to a larger reaction rate for the Si—OH surface relative to the Si—O—Si surface. This is attributed to the nature of the surface oxides; thermal oxidation is carried out at a high temperature, which anneals the film somewhat and generates stable surface Si—O—Si species. In contrast, processing of the ozone-oxidized samples occurs at lower temperature, resulting in a more hydrophilic and more reactive surface oxide. Thermal oxidation also creates a thicker oxide. This larger volume fraction of oxide present in the thermally oxidized material is responsible for the greater sensitivity observed at larger HF concentrations in FIG. 5. The relationship between oxide thickness and sensitivity was substantiated by optical determinations of the volume fraction of oxide in the films.

As-etched (Si—H) samples undergo a significantly smaller wavelength change when exposed to HF than either of the two oxide-based chemistries. This response is attributed to slow oxidation of the Si—H surface under the experimental conditions, followed by dissolution of the resulting surface oxide by $HF_{(aq)}$. Exposure to HF(aq) removes the surface oxide according to Eq. 1, and the remaining silicon surface is terminated with Si—H species. Samples submerged in solutions≥1.7% in HF for 10 min no longer display Si—O and Si—OH stretching bands in their FTIR spectra. Samples submerged in solutions containing <1.7% HF show increasing amounts of oxide with decreasing HF concentration in the ATR-FTIR spectrum, indicating incomplete removal of the oxide by HF.

FIGS. 6A-6D show the relative shift in wavelength of the main optical stop band peak reflected from ozone-oxidized porous Si rugate filters upon exposure to various concentrations of HF in water, as a function of time. Samples were submerged in deionized water followed by replacement with HF solution at time=0. From top to bottom: 6.8, 1.7, 0.46, and 0.11% HF. The data are presented as the measured wavelength maximum at the given time subtracted from the wavelength maximum at time=0 for each sample. All spectra were obtained from samples submerged in water (time<0) or the aqueous HF solution (time>0) at the indicated concentrations. Samples exposed to HF concentrations≥1.7% display two reaction phases. The first phase, indicated by a steep slope of the curves, is attributed to HF-induced dissolution of oxide species. The second phase, indicated by a more gradual slope, is attributed to the slow continual oxidation of the porous layer by water and dissolved oxygen, followed by attack and removal of the oxide species by HF. The amount of time needed to remove a quantity of silicon sufficient to blue shift the stop band by 63 nm is 10, 32, and 69 min for samples immersed in 13%, 0.86%, and 0.46% $HF_{(aq)}$, respectively. Therefore, lower concentrations of HF can be detected if the sample exposure time is increased.

Figures 6A, 6B, 6C, 6D:
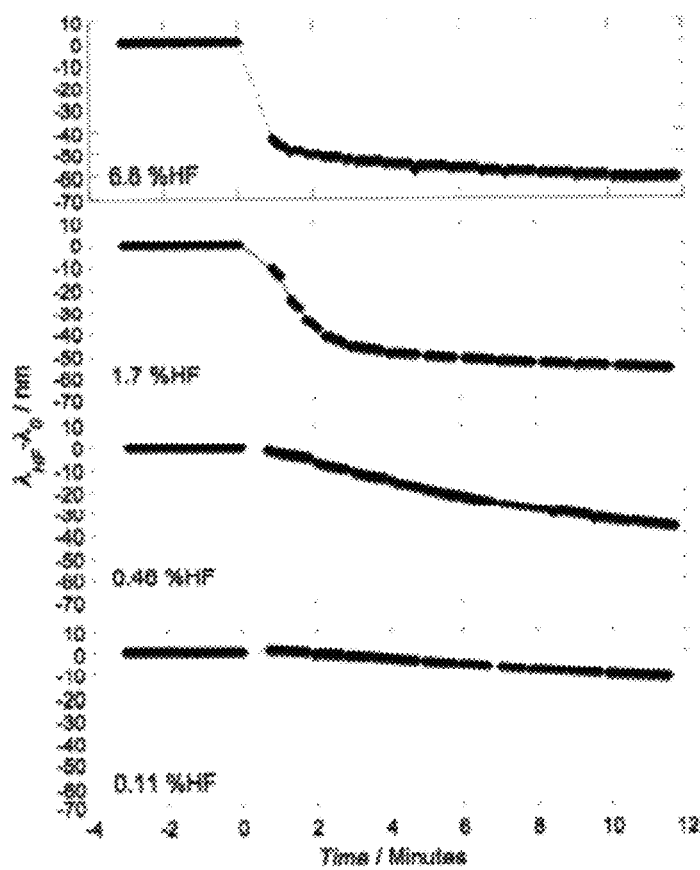
FIGS. 6A-6D show the relative shift in wavelength of the main optical stop band peak reflected from ozone-oxidized porous Si rugate filters upon exposure to various concentrations of HF in water, as a function of time.

The porosity of ozone-oxidized samples before and after 10 min. exposures to aqueous HF solutions was quantified by the gravimetric method and by calculated fits to the optical spectrum (Table 2). An increase in percent porosity is observed after exposure to HF. The porosity of samples exposed to 6.8 and 1.7% HF are almost identical. Examination of FIGS. 6A-6B show the two concentrations of HF produce similar Δλ (reflectance peak position) vs. time traces, indicating that the entire oxide component of the porous film has been removed within the 10 min. HF exposure period. The smaller increase in porosity observed for the samples exposed to 0.46 and 0.11% HF seen in FIGS. 6C-6D is consistent with the Δλ vs. time traces and indicative of incomplete removal of the oxide component.

TABLE 2

Porosity of Ozone-Oxidized Porous Si Rugate Samples
Before and After Exposure to HF$_{(aq)}$

| [HF]$^a$ | Gravimetric Porosity (%)$^b$ | Calculated Porosity (%)$^c$ |
|---|---|---|
| Before exposure | 59.8 ± 0.6 | 52.8 ± 0.3 |
| 6.8% | 84.4 ± 0.9 | 71.8 ± 0.6 |
| 1.7% | 83.1 ± 0.4 | 70.6 ± 0.1 |
| 0.46% | 76.6 ± 0.8 | 66.3 ± 0.8 |
| 0.11% | 63 ± 1 | 56.2 ± 0.9 |

$^a$Mass percentages HF in deionized water. All samples exposed to aqueous HF solutions at the indicated concentrations for 10 min.
$^b$Gravimetric measurement. Errors represent 1 standard deviation from 3 measurements.
$^c$Calculation based on a fit of the optical spectrum as described in section 2.5. Errors represent 1 standard deviation from 3 measurements.

Therefore, lower concentrations of HF can be detected if the sample exposure time is increased. Fits of the spectral reflectance data from samples exposed to HF required determination of the composite index of refraction of the porous layers. These layers contain three components: the HF-reactive oxide, the Si scaffolding, and the material filling the pores. Refractive index was calculated using a three-component Bruggemann approximation, according to Eq. 7:

$$V_{Si}\frac{n_{Si}^2 - n_{ps}^2}{n_{Si}^2 + 2n_{ps}^2} + V_{ox}\frac{n_{ox}^2 - n_{ps}^2}{n_{ox}^2 + 2n_{ps}^2} + (1 - V_{Si} - V_{ox})\frac{n_{fm}^2 - n_{ps}^2}{n_{fm}^2 + 2n_{ps}^2} = 0 \quad (7)$$

where $V_{Si}$ and $V_{ox}$ are the volume fractions of silicon and silicon dioxide in the porous matrix, respectively, $n_{fm}$ is the refractive index of the medium filling the pores (air or aqueous HF solution in this case, assumed to be wavelength-independent), $n_{Si}$ is the wavelength-dependent refractive index of the crystalline silicon, $n_{ox}$ is the wavelength-dependent refractive index of silicon dioxide, and $n_{ps}$ is the wavelength-dependent refractive index of the composite porous Si layer, incorporating all three components. This equation is similar to Eq. 3 that was used to calculate the reflectance spectra of FIG. 3, although the term $V_{Si}$ is defined differently. In Eq. 3, $V_{Si}$ is the volume of silicon that was present prior to oxidation. In Eq. 7 the term $V_{Si}$ simply represents the volume of silicon present in the composite film. The formulation of Eq. 7 is the more standard representation of the three-component Bruggeman expression.

By comparing the volume fraction terms before and after HF exposure it is possible to get information on the amount of both silicon and silicon dioxide removed during an HF exposure. The volume fraction of oxide removed from an Si—OH (ozone-oxidized) sample after 10-min exposure to HF solutions containing 0.11% and 0.46% is 3.0%±0.1% and 9.1%±1.1%, respectively. The total volume fraction of silicon oxide present in this type of film is 10.9%±0.6%. Thus at these two lower HF concentrations studied, the surface oxide is not completely removed in 10 min. Exposure of samples to solutions containing higher HF concentrations (1.7% and 6.8%) results in the complete removal of the oxide layer for the ozone-oxidized samples. In addition, the optical fits indicate that these higher two HF concentrations also remove a volume fraction of silicon corresponding to 7.5%±0.2% and 8.6%±0.4%, respectively. The total volume fraction of oxide in the films is 36.8%±0.4%. The volume fraction of oxide in the thermally oxidized samples (Si—O—Si) is significantly greater (40.3%±0.6%), leading to the greater sensitivity at high HF concentrations relative to the Si—OH surface chemistry. Thus, the optical calculations agree with the mechanistic theory that the response of the sensor is controlled by removal of silicon oxide in a fast step and removal of elemental silicon in a slower step. This interpretation accounts for the continual slow blue shift observed at longer exposure times.

A portion of the porous matrix of the sensors in the experiments was filled with polystyrene as a fiducial marker. This polymer is not attacked by HF or Cl, in the time frame of the experiments, and so it provides a chemically stable optical reference that allows more accurate means to follow the reactions of HF or $Cl_2$ with the open portions of the sensor. The fiducial marker also provides the ability to correct for the dependence of the spectrum on probing angle. The spectrum reflected from a porous Si multilayer film is related to the angle at which the spectrum is acquired, as described by Eq. 8:

$$m\lambda = 2nd \cos\theta \quad (8)$$

where m is the order of reflection, λ is the incident wavelength, n is the refractive index of the film at λ, d is the physical thickness of each layer, and θ is the angle between the light source and a vector normal to the plane of the Si wafer. For observation at normal incidence, θ=0 and the equation reduces to mλ=2nd. In equation (8), for all values of θ, the detector is assumed to be along the specular reflection axis relative to the light source.

Figure 7A:
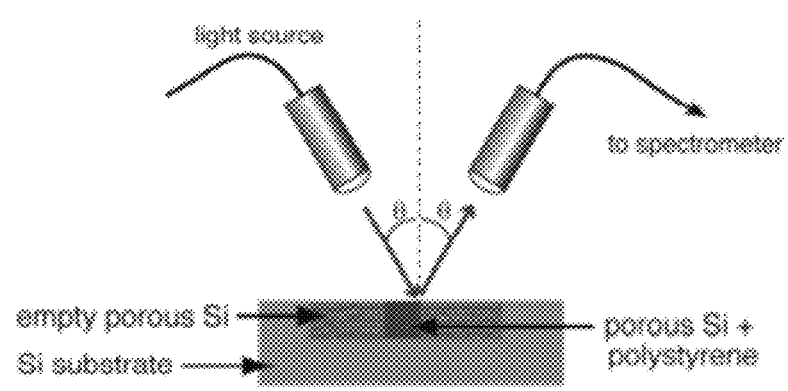
FIG. 7A illustrates an experimental set up used to test a sensor of the invention with a fiducial marker at various angles.
Figure 7B:
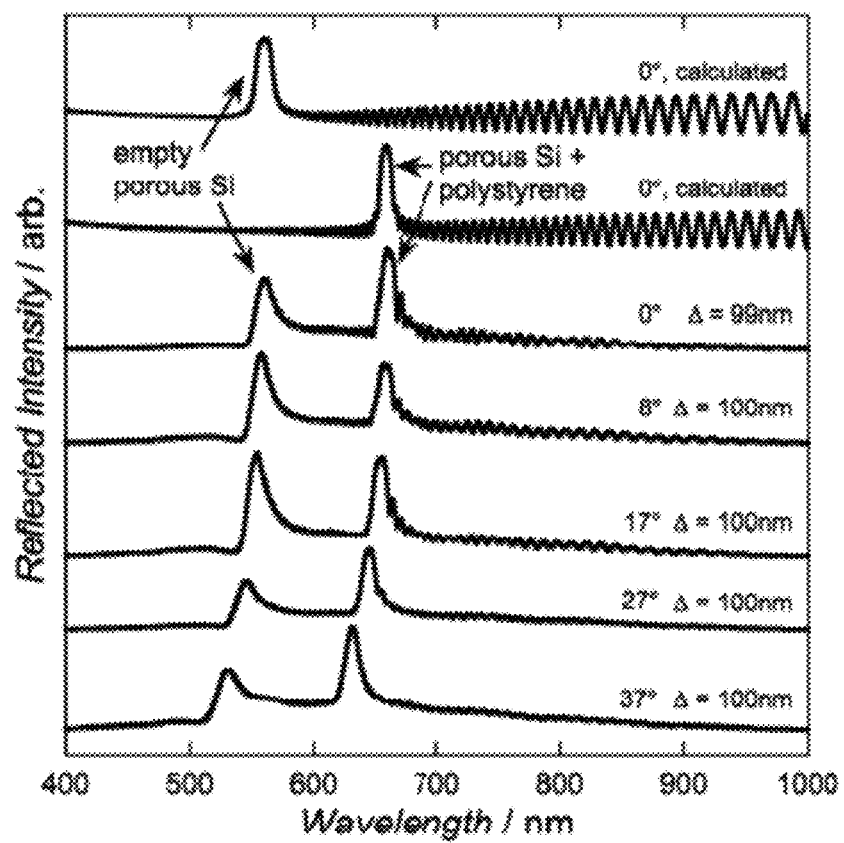
FIGS. 7B and 7C, show calculated and experimental reflectance spectra as a function of observation angle for an ozone-oxidized porous Si (pSi) sample containing a polystyrene fiducial marker.
Figure 7C:
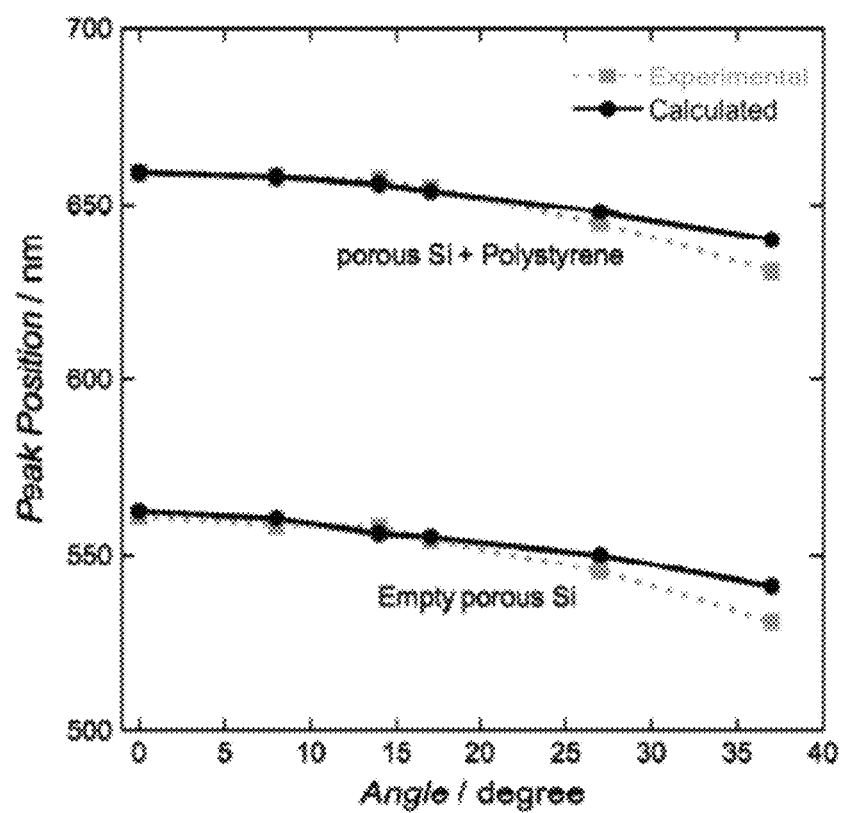

A sensor of the invention was tested in the experimental set up shown in FIG. 7A to determine its ability to compensate for off-specular axis measurements. FIGS. 7B and 7C show the calculated and experimental reflectance spectra as a function of observation angle for an ozone-oxidized porous Si (pSi) sample containing a polystyrene fiducial marker. The experimental optical setup is shown in (A). Plot (B) shows (from top to bottom): theoretical reflectance spectrum from empty porous Si obtained at normal incidence (θ=0 degrees); theoretical reflectance spectrum from polystyrene-filled porous Si obtained at normal incidence (θ=0 degrees); experimental spectra obtained at θ=0, 8, 17, 27 and 37 degrees. The spectrometer spot was set sufficiently large that it probed both the empty and the polystyrene-filled regions of the chip simultaneously. Δ indicates the difference between the wavelengths of the reflectance peak maxima of the pSi+polystyrene and the empty pSi peaks. Absolute wavelengths of the reflectance peak maxima are listed in Table 3. Spectra are normalized to the intensity of the pSi+polystyrene peak. (C) Experimental and calculated wavelengths of the reflectance peak maxima for empty and for polystyrene-filled pSi as a function of θ for θ=0, 8, 14, 17, 27 and 37 degrees.

TABLE 3

Wavelengths ($\lambda_{max}$) of reflectance peaks measured from an ozone-oxidized porous Si sample containing a polystyrene fiducial marker as a function of probing angle.

| Probing Angle, degrees$^a$ | $\lambda_{max}$ of empty region, nm | $\lambda_{max}$ of polystyrene-filled region, nm | Difference, nm$^b$ |
|---|---|---|---|
| 0 | 560 | 659 | 99 |
| 8 | 558 | 658 | 100 |
| 14 | 557 | 657 | 100 |
| 17 | 554 | 654 | 100 |
| 27 | 545 | 645 | 100 |
| 37 | 531 | 631 | 100 |

$^a$Relative to surface normal, defined in FIG. 6a.
$^b$Defined as λ (ps) − λ (empty), where λ (ps) and λ (empty) are the wavelengths of the reflectance peaks corresponding to the polystyrene-filled and the empty regions of the ozone-oxidized porous Si rugate filter, respectively.

The wavelength of the reflectance peak decreases at probing angles off of normal incidence. This property adds an extra variable that must be considered when analyzing sensor response. The angular dependence is particularly problematic in a remote sensing configuration, where the angle between the light source and the face of the porous Si chip cannot necessarily be fixed. The polystyrene fiducial marker provides a second reflectance peak that can be used to correct for angular fluctuations, as seen in the data of FIGS. 7B and 7C.

The angle-resolved calculated and experimental spectra for a porous Si-based rugate filter that contains both empty and polystyrene-filled regions are given in FIGS. 7B and 7C. Experimental data were acquired from three samples at angular values of θ=0, 8, 14, 17, 27 and 37 degrees. The blue shift in wavelength with increasing angle follows the relationship of Eq. 8, such that the difference $\lambda_{max}$(polymer)−$\lambda_{max}$(empty) is a constant value (100 nm for the samples in the present case).

The calculated angle-resolved reflectance spectra take into account the different oxide volumes of empty and polystyrene-filled porous Si. The thermal post-treatment used to prepare the ozone-oxidized porous Si samples (180° C. in air for 30 min) results in an increase of the oxide volume. Due to the masking effect of the polymer, the polystyrene-filled region of the porous Si sample is not oxidized as effectively and only the volume of oxide originating from the ozone oxidation step has to be considered in calculations. Calculated reflectance spectra at normal incidence of empty and polystyrene-filled porous silicon are reported together with the experimental spectra (FIG. 7B), and the experimental and calculated wavelengths ($\lambda_{max}$) of the resonance peak vs. incidence angle are compared (FIG. 7C). The calculations agree well with the experimental results the reflectance peak position of both empty and polystyrene-filled porous Si blue shift by similar amounts for each probing angle. Thus the quantity Δ, defined as $\lambda_{max}$(polymer)−$\lambda_{max}$(empty), is a constant value. Although a slight discrepancy between the calculated and experimental peak wavelengths is observed at probing angles>17 degrees, neither the experimental nor the calculated values of Δ deviate from the fixed value of 100 nm for all angles studied. The discrepancy is attributed to the lower accuracy with which incident and reflected angles can be measured on the experimental setup used for these measurements.

Figure 8:
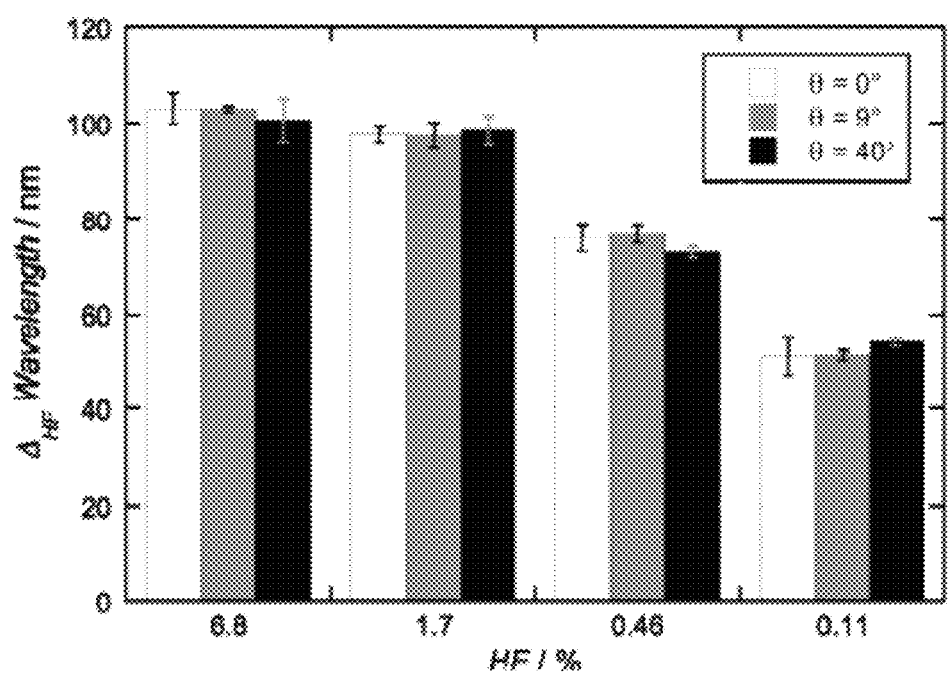
FIG. 8 shows the shift in wavelength, relative to a fiducial marker, of the reflectance peak maximum from ozone-oxidized porous Si samples (Si—OH) after 10 min. exposure to the indicated mass percentage concentrations of $HF_{(aq)}$.

Ozone-oxidized samples containing polystyrene fiducial markers were exposed to aqueous HF solutions at concentrations of 6.8, 1.7, 0.46 and 0.11% for 10 min, and reflectance peak positions were monitored at 3 probing angles: 0, 9 and 40 degrees from normal incidence. FIG. 8 shows shift in wavelength, relative to a fiducial marker, of the reflectance peak maximum from ozone-oxidized porous Si samples (Si—OH) after 10 min. exposure to the indicated mass percentage concentrations of $HF_{(aq)}$. Values measured at the indicated probing angles θ, as defined in FIG. 7A, are compared. The fiducial marker in the experiments consists of a small region on each porous Si sample that is filled with inert polystyrene, which provides a reflectivity peak at a wavelength, $\lambda_0$(ps), that is different from the wavelength of the solution-filled regions of the HF exposed porous Si film, $\lambda_{HF}$(aq). $\Delta_{HF}$ Wavelength is defined as $\lambda_0$(ps)−$\lambda_{HF}$(aq). The initial value, of $\Delta_0$ Wavelength, at 0% $HF_{(aq)}$ is ~43 nm. Representative spectra at 0% $HF_{(aq)}$ are shown in FIG. 7B; numeric data are provided in Table 4. Data represent the average of 4-5 samples. Error bars indicate one standard deviation. All measurements were obtained with samples still immersed in the aqueous solutions.

TABLE 4

One representative sample data set of wavelengths (λ) of reflectance peaks measured from an ozone-oxidized porous Si sample containing a polystyrene fiducial marker as a function of probing angle and HF exposure.

| | Probing angle[a] | | | | | | | | | | | |
|---|---|---|---|---|---|---|---|---|---|---|---|---|
| | 0 degrees | | | | 9 degrees | | | | 40 degrees | | | |
| % $HF_{(aq)}$ | λ (ps) nm | $\lambda_0$ (aq) nm | $\lambda_{HF}$ (aq) nm | $\Delta_{HF}$ $(\Delta_0)_b$ nm | λ (ps) nm | $\lambda_0$ (aq) nm | $\lambda_{HF}$ (aq) nm | $\Delta_{HF}$ $(\Delta_0)_b$ nm | λ (ps) nm | $\lambda_0$ (aq) nm | $\lambda_{HF}$ (aq) nm | $\Delta_{HF}$ $(\Delta_0)_b$ nm |
| 0.11 | 689 | | 638 | 51 | 666 | 620 | 614 | 52 | 727 | 682 | | 55 |
| | | 650 | | (39) | | | | (46) | | | 672 | (45) |
| 0.46 | 700 | | 624 | 76 | 678 | 632 | 600 | 78 | 709 | 666 | | 74 |
| | | 658 | | (42) | | | | (46) | | | 635 | (43) |
| 1.7 | 696 | | 598 | 98 | 678 | 633 | 580 | 98 | 643 | 600 | | 99 |
| | | 653 | | (43) | | | | (45) | | | 544 | (43) |
| 6.8 | 689 | | 585 | 104 | 682 | 635 | 578 | 104 | 638 | 595 | | 102 |
| | | 648 | | (41) | | | | (47) | | | 536 | (43) |

Samples probed at 40 degrees were etched on the roughened side of the Si wafer to promote scattering of light. SEM measurements indicated that the porous layer etched on the roughened side of the wafer has the same overall thickness and spatial porosity modulation as one etched on the polished side. The porosity as measured by the gravimetric method is also the same. The value of $\lambda_{max}$ for the aqueous HF solution-filled region of the chip shifts to the blue with increasing HF concentration. By contrast, the value of $\lambda_{max}$ for the polymer-filled region of the chip does not change at any value of HF concentration studied. Correspondingly, the value of Δ (difference between the two reflectance peak wavelengths) increases with increasing HF concentration as seen in FIG. 8.

Figure 9:
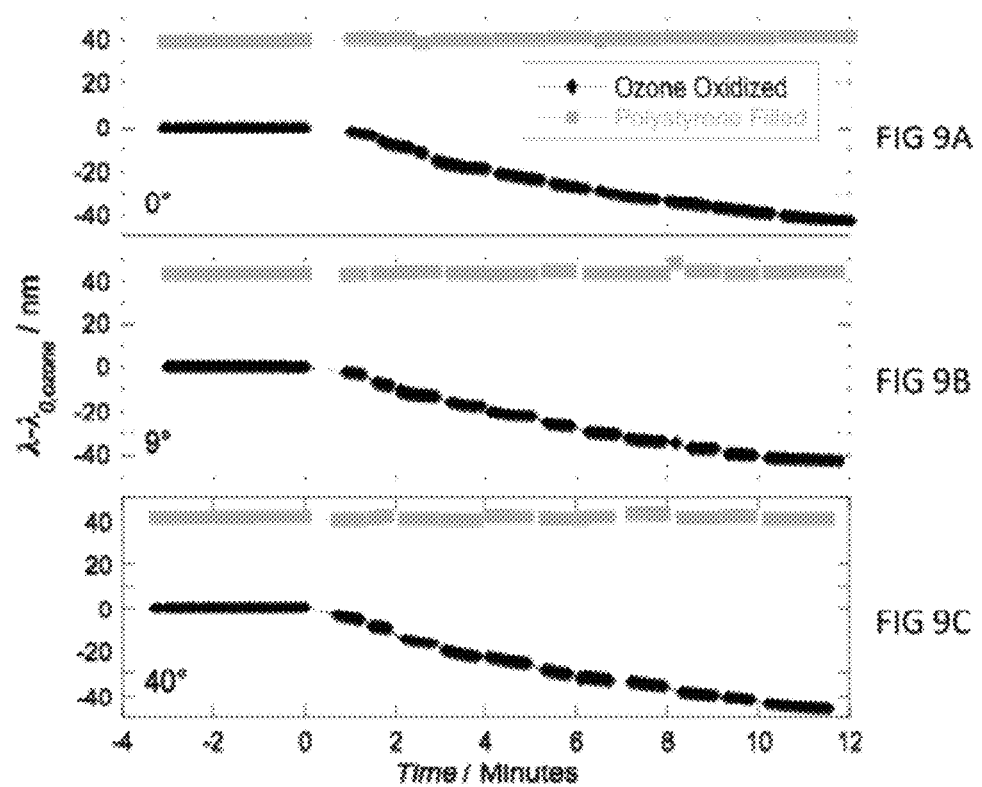
FIGS. 9A-9C plot shift in wavelength of the maximum of the reflectance peak measured from the reactive-open (black diamond) and polystyrene-filled (gray square) regions of an ozone-oxidized porous Si sample, as a function of time exposed to 0.46% $HF_{(aq)}$ for measurement angles of 0°, 9° and 40°.

FIG. 8 shows the shift in wavelength, relative to a fiducial marker, of the reflectance peak maximum from ozone-oxidized porous Si samples (Si—OH) after 10 min. exposure to the indicated mass percentage concentrations of $HF_{(aq)}$. The polystyrene fiducial marker provides a reflectivity peak at a wavelength, $\lambda_0$(ps), that is different from the wavelength of the solution-filled regions of the HF exposed porous Si film, $\lambda_{HF}$(aq). $\Delta_{HF}$ Wavelength is defined as $\lambda_0$(ps)−$\lambda_{HF}$(aq). The initial value, of $\Delta_0$ Wavelength, at 0% $HF_{(aq)}$ is ~43 nm. Representative spectra at 0% $HF_{(aq)}$ are shown in FIG. 7B; numeric data are provided in Table 4. Data represent the average of 4-5 samples. Error bars indicate one standard deviation. All measurements were obtained with samples still immersed in the aqueous solutions For a given concentration of HF, the quantity Δ is the same for all angles probed. Plots of $\lambda_{max}$ vs time for the solution-filled and for the polystyrene-filled porous Si regions are provided in FIGS. 9A-9C. Specifically, FIGS. 9A-9C plot shift in wavelength of the maximum of the reflectance peak measured from the reactive-open (black diamond) and polystyrene-filled (gray square) regions of an ozone-oxidized porous Si sample, as a function of time exposed to 0.46% $HF_{(aq)}$, for measurement angles of 0°, 9° and 40°. Results indicate that the angle of incidence does not significantly affect the separation between the reflectance peak maximum of porous silicon and the polystyrene filled fiducial marker, meaning the fiducial marker reduces errors that would result from measurement angle changes. The results show that a polystyrene-infused porous Si fiducial allows the sensor response to be separated from the effects of probing angle. Subtraction of the reflectance peak wavelength of the ozone oxidized, aqueous solution-filled region of the porous Si sample from the polystyrene-filled, nonreactive region results in a difference ("$\Delta_0$ Wavelength" in Table 4) of ~43 nm at all probing angles before introduction of HF. The increasing positive value of the quantity "$\Delta_{HF}$ Wavelength" (FIG. 8) with increasing HF concentration corresponds to a spectral blue shift of the reactive, ozone-oxidized porous Si photonic crystal.

Experiments also tested the ability of the surface chemistries (Si oxide and Si—H) for their relative insensitivity to cross-talk with the two analytes studied (HF and $Cl_2$); Si—O—Si and Si—OH were not expected to react with $Cl_9$ and Si—H is not expected to react with HF. The reaction of the Si—H surface of porous Si with $Cl_2$ could proceed via attack at both Si—Si and Si—H bonds, although prior studies have indicated that halogens attack Si—Si bonds more readily than Si—H bonds on porous Si surfaces (Eq. 9). Studies of the reactivity of the Si—Cl species on Si (111) and (100) surfaces indicate that hydrolysis generates Si—O—Si (Eq. 10) in preference to Si—OH.

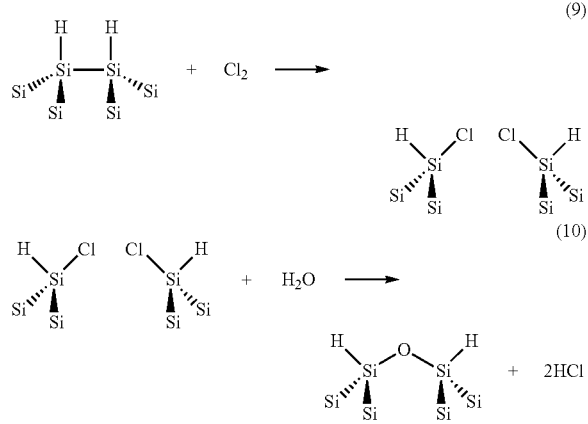

Chlorine used in the experiments was produced by acidification of sodium hypochlorite solutions followed by washing with Millipore water to remove HCl. The three surface chemistry types (as-etched, ozone-oxidized and furnace-oxidized at 600° C.) were exposed to chlorine gas in an air tight vessel filled with laboratory air. Reflectance spectra were recorded for 10 min prior to, and for 30 min after, introduction of $Cl_2(g)$.

All surface chemistry types exhibited an instantaneous red shift in the spectral reflectance peak of several nm upon introduction of the $Cl_2$ analyte. The red shift is attributed to water vapor contained in the analyte matrix; an increase in relative humidity produces a spectral red shift for most porous Si surface chemistries due to water adsorption. The reflectance peaks from the ozone-oxidized and furnace-oxidized samples stabilize relatively quickly and exhibit no further change under the experimental conditions. The as-etched samples, however, display a rapid blue shift of the reflectance peak, indicative of the oxidation and hydrolysis reactions shown in Eqs 9 and 10.

Figure 10:
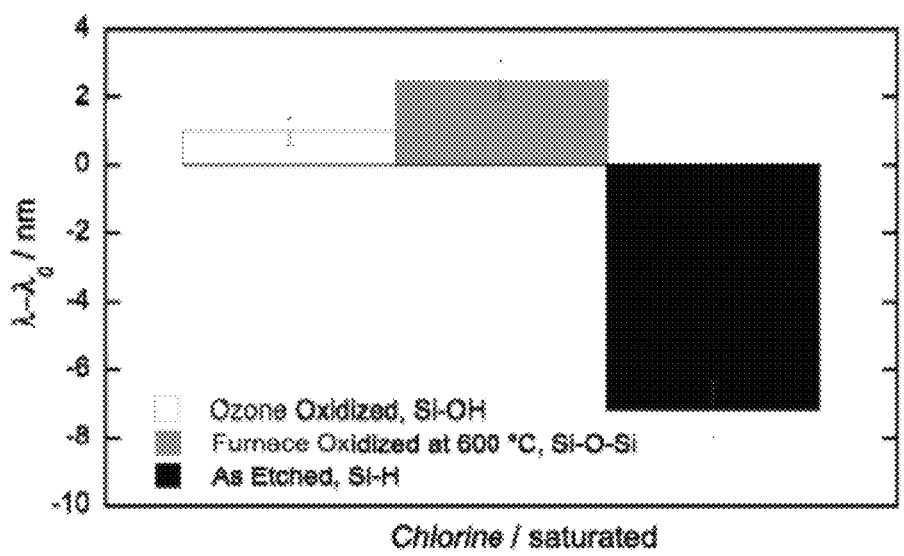
FIG. 10 shows the shift in wavelength of the porous Si reflectance peak position after 30 min. of continuous exposure to $Cl_2$ gas in humid air.

FIG. 10 shows the shift in wavelength of the porous Si reflectance peak position after 30 min. of continuous exposure to $Cl_2$ gas in humid air. Spectra were obtained in situ, without removing the samples from the $Cl_2$/air chamber. Three sample types are presented: ozone-oxidized (white bar), furnace-oxidized at 600° C. (gray bar) and as-etched (hydride terminated) porous Si (black bar). Data represent the average of 5 samples with one standard deviation error bars.

FIGS. 11A-11C shows the ATR-FTIR spectrum of as-etched porous Si after exposure to chlorine for 30 min. displays Si—O and Si—OH bands characteristic of silicon oxide and of surface-adsorbed water, respectively. Exposure of as-etched porous Si to dry $Cl_2$ in a $N_2$ atmosphere also produces a spectral blue shift, although the magnitude of the blue shift is smaller than when water vapor and oxygen are present. ATR-FTIR spectra of ozone- and furnace-oxidized samples show no detectable change after chlorine exposure.

Thus, preferred ozone oxidized sensors of the invention provide sensitive HF detection. Direct comparison of gas phase with liquid-phase measurements is not exact, but the concentrations of HF detected by preferred sensors and methods are significantly larger than the gas-phase work discussed in the background. The lowest concentration tested in experiments discussed above is 0.11% by mass, which corresponds to 1100 ppm. However, the timescale of the present experiments is significantly shorter than in the prior methods discussed in the background (10 min vs. 4-48 h). It is expected that longer exposure times will yield lower limits of detection. The fundamental response depends on the stoichiometric quantity of HF that has reacted with the sensor element, and the time-dependence of this response must be taken into account in order to yield quantitative results.

As shown in the experimental data preferred sensors of the invention provide a fiducial marker that can reduce zero point drift due to humidity changes and can compensate for changes in observation angle. The ability to probe the sensor with a remote optical detector, without the need to physically collect the specimen after analyte exposure, is a key need for many remote monitoring applications.

The inert fiducial marker in preferred porous sensors and sensing methods creates a self-referenced sensor that can be probed with a free-space optical detector, and can also be monitored by simple visual observations. The fiducial marker generates a separate, chemically stable reflectance peak in reflectance spectra that acts as an internal standard, eliminating zero point drift associated with variable sample-optics angles. Zero point drift related to humidity can also be compensated. In preferred sensors, because of the specificity of the chemical reactions used to prepare the porous silicon for HF and $Cl_2$ analytes (silicon oxide for $HF_{(aq)}$ and silicon hydride for $Cl_{2(g)}$), minimal analyte cross reactivity is observed between the two sensor types.

Coating the nanoengineered silicon photonic crystals with the appropriate molecules can also produce assay devices for many important classes of enzymes (proteases, RNAase, DNAase, etc.). The system is suitable to detect the activity of any enzyme and other catalytic or noncatalytic analytes of interest that can degrade a substrate carried by the porous optical sensor. Because the mode of action of chloramines is to react with lipids and other biological species comprising the protective machinery of bacteria, biopolymer coatings that possess a specific reactivity with chloramines can be evaluated. Films can also contain a region that is protected with an unreactive polymer providing a fiducial marker, which allows quick evaluation of the sensor by visual comparison of the color of the two spots on the chip.

In a preferred embodiment, the reactive surface type used to detect triggered oxidation is hydrophobic surface that contains surface hydrides. These species, though kinetically stable in air, are rapidly degraded in corrosive environments (e.g. ozone, $NO_x$). This surface type will is also expected to be responsive to chloramines.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A porous sensor, comprising nanoporous material that is reactive towards a chemical or biological analyte(s) of interest and, within the nanoporous material a region of pores that are filled with an inert fiducial marker that is substantially non reactive towards the chemical or biological analyte of interest, wherein the region of pores are filled such that the region of pores provides a constant response that will not drift with changing humidity or in the presence of analytes including the biological analyte(s) of interest.

2. The porous sensor of claim 1, wherein the nanoporous material comprises nanoporous silicon.

3. The porous sensor of claim 2, wherein the fiducial marker comprises an inert polymer.

4. The porous sensor of claim 3, wherein the inert polymer comprises polystyrene.

5. The porous sensor of claim 1, wherein the fiducial marker comprises one of an organic polymer or polymer blend, a biopolymer or biopolymer blend, an organic compound or compounds, an inorganic compound or compounds, or a mixture of more than one of the preceding compounds.

6. The porous sensor of claim 1, wherein the nanoporous material that is reactive has a reactive surface hydride or mixed surface hydride/alkane and the anlayte comprises chloramines.

7. The porous sensor of claim 1, wherein the nanoporous material that is reactive comprises ozone oxidized porous material that the analyte comprises HF.

8. The porous sensor of claim 1, wherein the nanoporous material that is reactive has a reactive oxide surface.

9. The porous sensor of claim 1, wherein the nanoporous material that is reactive has a reactive hydride surface.

10. A method of analyte sensing, the method comprising:
introducing suspected analyte to a reactive nanoporous layer including a fiducial marker region including pores that are filled with an inert fiducial marker that is substantially non reactive to the suspected analyte, wherein the region of pores are filled such that the region of pores provides a constant response that will not drift with changing humidity or in the presence of analytes including the biological analyte(s) of interest;
observing the reactive nanoporous layer and the fiducial marker region;
determining the presence or absence of analyte based upon a change in reflection of the reactive nanoporous layer and the fiducial marker region.

11. The method of claim 10, wherein said observing comprises human observation and the change in reflection comprises a color change.

12. The method of claim 10, wherein said observing comprises illuminating both the reactive nanoporous layer and the fiducial marker and sensing the resulting reflectance spectrum, and said determining comprises determining an amount of peak shift between a reflectance peak of the reactive nanoporous layer and a reflectance peak of the fiducial marker.

13. The method of claim 10, wherein the fiducial marker comprises one of an organic polymer or polymer blend, a biopolymer or biopolymer blend, an organic compound or compounds, an inorganic compound or compounds, or a mixture of more than one of the above compounds.

14. The method of claim 10, wherein the reactive nanoporous layer has a reactive surface hydride or mixed surface hydride/alkane and the anlayte comprises chloramines.

15. The method of claim 10, wherein the reactive nanoporous layer comprises ozone oxidized porous material that the analyte comprises HF.

16. The method of claim 10, wherein the reactive nanoporous layer has a reactive oxide surface.

17. The method of claim 10, wherein the reactive nanoporous layer has a reactive hydride surface.

18. The method of claim 10, wherein the reactive nanoporous layer has a surface exposing free pores that accept analyte and an area that is filled with the fiducial marker and said observing comprises illuminating a portion of the surface including both the exposed free pores and the area that is filled.

19. A porous sensor, consisting of nanoporous material that is reactive toward a chemical or biological analyte(s) of interest and fiducial marker material infused into pores in only a portion of the nanoporous material such that the fiducial material fully occupies the depth of the pores in the portion of the nanoporous material, wherein the fiducial marker material is an inert fiducial marker that is substantially non reactive towards the chemical or biological analyte of interest and wherein the fiducial material leaves remaining regions of the nanoporous material free to accept analyte within pores that have no fiducial marker material therein.

20. The sensor of claim 19, wherein a surface of the sensor provides free pores to accept analyte except in an area in the portion of the nanoporous material that is infused with the fiducial marker material.

21. The sensor of claim 19, wherein the nanoporous material that is reactive has a reactive surface hydride or mixed surface hydride/alkane and the anlayte comprises chloramines.

22. The sensor of claim 19, wherein the nanoporous material that is reactive is ozone oxidized porous material and the analyte comprises HF.

23. The sensor of claim 19, wherein the nanoporous material that is reactive has a reactive oxide surface.

24. The sensor of claim 19, wherein the nanoporous material that is reactive has a reactive hydride surface.

* * * * *

UNITED STATES PATENT AND TRADEMARK OFFICE
CERTIFICATE OF CORRECTION

PATENT NO. : 8,778,690 B2
APPLICATION NO. : 13/222957
DATED : July 15, 2014
INVENTOR(S) : Michael J. Sailor et al.

It is certified that error appears in the above-identified patent and that said Letters Patent is hereby corrected as shown below:

In the Specification:

| | |
|---|---|
| Col. 4, line 8 | Before "inert" please delete "a" and insert --an-- therefor. |
| Col. 6, line 28 | After "B-doped)" please delete "was". |
| Col. 9, line 10 | Please delete "$Si_6^{2-}$" and insert --$SiF_6^{2-}$-- therefor. |
| Col. 10, line 43 | After "$n_{Si}$" please delete the ";". |
| Col. 10, line 51 | After "$V_{Si}$" please delete the ";". |
| Col. 11, line 20 | After "$V_S$" please delete the ";". |
| Col. 16, line 8 | Please delete "C1" and insert --$Cl_2$-- therefor. |
| Col. 19, line 31 | Please delete "$Cl_9$" and insert --$Cl_2$-- therefor. |
| Col. 21, line 16 | After "type" please delete "will". |

In the Claims:

| | |
|---|---|
| Claim 7, Col. 21, line 54 | Please delete "that" and insert --and-- therefor. |
| Claim 15, Col. 22, line 26 | Please delete "that" and insert --and-- therefor. |

Signed and Sealed this
Seventh Day of April, 2015

Michelle K. Lee
*Director of the United States Patent and Trademark Office*